Figure 1A:
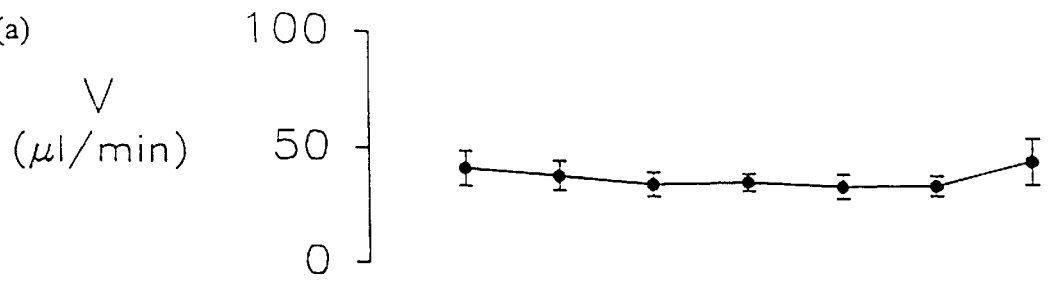

US005859043A

United States Patent [19]

Kapusta

[11] Patent Number: 5,859,043
[45] Date of Patent: Jan. 12, 1999

[54] METHOD FOR MAINTAINING KIDNEY FUNCTION DURING SURGERY OR SEVERE TRAUMA UNDER GENERAL ANESTHESIA

[75] Inventor: Daniel R. Kapusta, Slidell, La.

[73] Assignee: Board of Supervisors of Louisiana State University and Agricultural and Mechanical College, Baton Rouge, La.

[21] Appl. No.: 810,832

[22] Filed: Mar. 6, 1997

Related U.S. Application Data

[60] Provisional application No. 60/042,272 Jun. 11, 1996.
[51] Int. Cl.$^6$ .................................................. A61K 31/40
[52] U.S. Cl. ............................................................ 514/409
[58] Field of Search ..................................... 514/183, 409

[56] References Cited

U.S. PATENT DOCUMENTS

| | | |
|---|---|---|
| 4,663,343 | 5/1987 | Horwell et al. ........................ 514/429 |
| 4,888,355 | 12/1989 | Clemence et al. ..................... 514/429 |
| 4,891,379 | 1/1990 | Zimmerman et al. .................. 514/315 |
| 4,906,655 | 3/1990 | Horwell et al. ........................ 514/422 |
| 4,965,278 | 10/1990 | Horwell et al. ........................ 514/414 |
| 4,988,727 | 1/1991 | Clemence et al. ..................... 514/422 |
| 4,992,450 | 2/1991 | Zimmerman et al. .................. 514/315 |
| 5,019,588 | 5/1991 | Horwell et al. ........................ 514/409 |
| 5,063,242 | 11/1991 | Horwell et al. ........................ 514/414 |
| 5,064,834 | 11/1991 | Zimmerman et al. .................. 514/279 |
| 5,068,244 | 11/1991 | Moura et al. ........................... 514/428 |
| 5,116,842 | 5/1992 | Naylor et al. .......................... 514/252 |
| 5,130,329 | 7/1992 | Moura et al. ........................... 514/429 |
| 5,317,028 | 5/1994 | McKnight et al. ..................... 514/409 |
| 5,319,087 | 6/1994 | Zimmerman et al. .................. 546/240 |
| 5,369,105 | 11/1994 | McKnight et al. ..................... 514/212 |
| 5,384,113 | 1/1995 | Deutsch et al. ........................ 424/1.69 |
| 5,422,356 | 6/1995 | Zimmerman et al. .................. 514/317 |

OTHER PUBLICATIONS

Salas et al., J. Pharmac. Exp. Ther. 262(3), 979–86 (1992).
Salas et al., J. of Pharmacology and Experimental Therapeutics, 250:992–999, 1989.
Y. Hamaya et al., "Diuretic Effect of Clonidine during Isoflurane, Nitrous Oxide, and Oxygen Anesthesia," Anesthesiology, vol. 81, pp. 811–819 (1994).
G. Slizgi et al., "Effects of the Highly Selective Kappa Opioid, U–50,488, on Renal Function in the Anesthetized Dog," J. Pharmacol. Exp. Ther., vol. 230, pp. 641–645 (1984).
G. Peters et al., "Diuretic Actions in Man of a Selective Kappa Opioid Agonist: U–62,066E," J. Pharmacol. Exp. Ther., vol. 240, pp. 128–131 (1987).
G. Rimoy et al., "The Cardiovascular and Central Nervous System Effects in the Human of U–62,066E," Eur. J. Clin. Pharmacol, vol. 46, pp. 203–207 (1994).

D. Brooks et al., "Opiate Receptors in the Blood–Brain Barrier Mediate Kappa Agonist–Induced Water Diuresis," J. Pharmacol. Exp. Ther., vol. 266, pp. 164–171 (1993).
D.R. Bevan et al., "Renal Function During and After Anaesthesia and Surgery: Significance for Water and Electrolyte Management," Brit. J. Anaesth., vol. 45, pp. 968–975 (1973).
Kapusta, "Opioid Mechanisms Controlling Renal Function," Clin. Exp. Pharmacol. Physiol. vol. 22, pp. 891–902 (1995).
N. Ashton, "κ–Opioid–Receptor Agonists Modulate the Renal Excretion of Water and Electrolytes in Anaesthetized Rats," Br. J. Pharmacol., vol. 99, pp. 181–185 (1990).
P. Reece et al., "Diuretic Effects, Pharmacokinetics, and Safety of a New Centrally Acting Kappa–Opioid Agonist (CI–977) in Humans," J. Clin. Pharmacol., vol. 34, pp. 1126–1132 (1994).
D. Kapusta et al., "Role of Renal Nerves in Excretory Responses to Administration of Kappa Agonists in Conscious Spontaneously Hypertensive Rats," J. Pharmacol. Exp. Ther., vol. 251, pp. 230–237 (1989).
D. Kapusta et al., "Central Kappa Opioid Receptor–Evoked Changes in Renal Function in Conscious Rats: Participation of the Renal Nerves," J. Pharmacol. Exp. Ther., vol. 267, pp. 197–204 (1993).
D. Kapusta et al., "Central Kappa Opioids Blunt the Renal Excretory Responses to Volume Expansion by a Renal Nerve–Dependent Mechanism," J. Pharmacol. Exp. Ther., vol. 273, pp. 199–205 (1995).
G. Rimoy et al., "Mechanism of diuretic action of spiradoline (U–62,066E)—a Kappa Opioid Receptor Agonist in the Human," Br. J. Clin. Pharmac., vol. 32, pp. 611–615 (1991).

*Primary Examiner*—Phyllis G. Spivack
*Attorney, Agent, or Firm*—John H. Runnels

[57] ABSTRACT

Kappa-opioid agonists prevent the impairment of renal function otherwise caused by the combination of gaseous anesthesia and surgery or severe trauma. Not only do these agents preserve renal function and maintain urine output, they also maintain plasma electrolyte concentration and osmolality by reducing renal loss of sodium and potassium when compared to other diuretic agents. The preservation of urine flow as well as the ability to retain body sodium, potassium, calcium, and osmolality during surgery or severe trauma under gaseous anesthesia are novel and unique properties associated only with kappa opioid agonists. To date, no other clinically-used diuretic agent has been shown to provide constant urine flow, or to retain electrolytes during anesthesia and surgery. The kappa opioid agonists may be used in surgical patients with normal cardiovascular function, but are particularly useful in patients with compromised cardiovascular and/or renal function.

16 Claims, 15 Drawing Sheets

Fig. 3(a) V (μl/min)
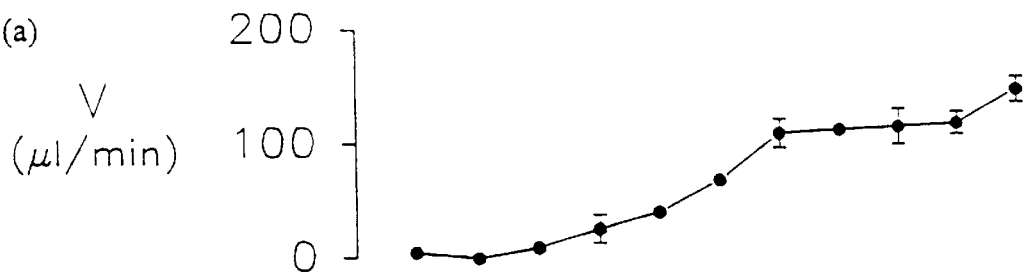
Fig. 3(b) $U_{Na}V$ (μeq/min)
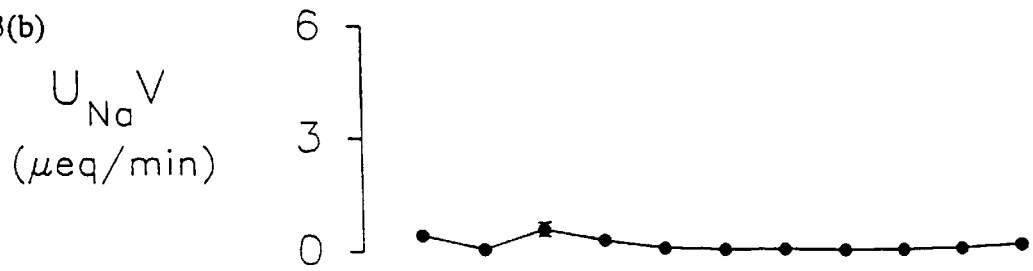
Fig. 3(c) $U_KV$ (μeq/min)
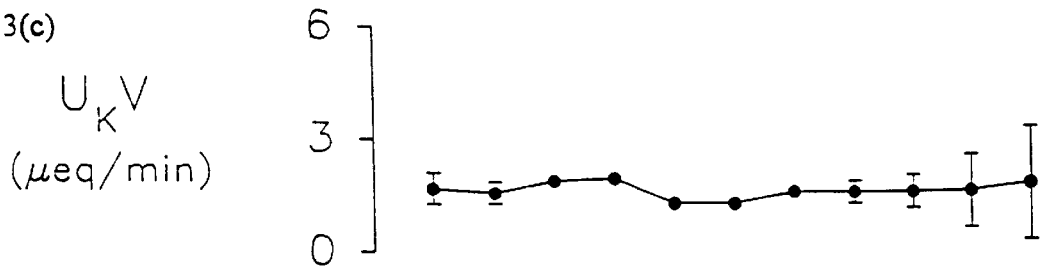
Fig. 3(d) $V_{Osm}$ (mosm/L $H_2O$)
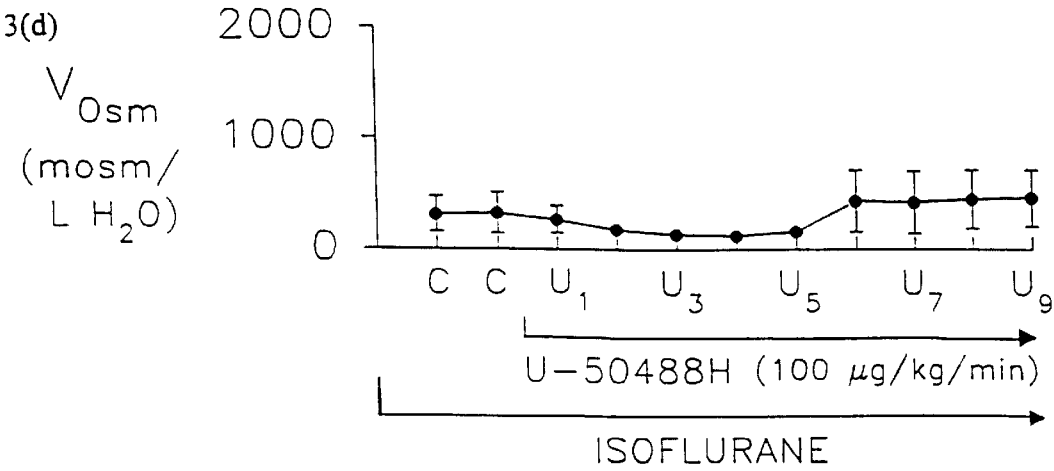
U-50488H (100 μg/kg/min)
ISOFLURANE

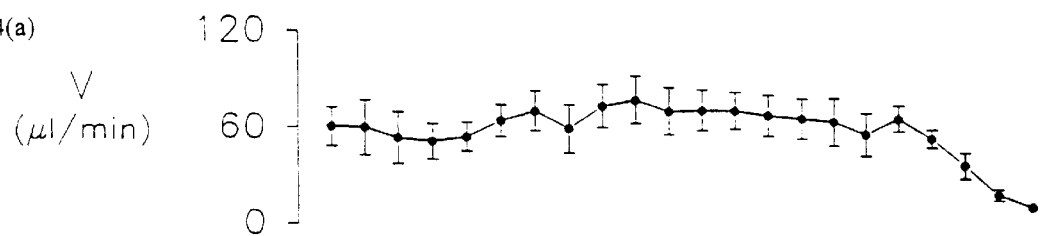
Fig. 4(a) V (μl/min)
Fig. 4(b) $U_{Na}V$ (μeq/min)
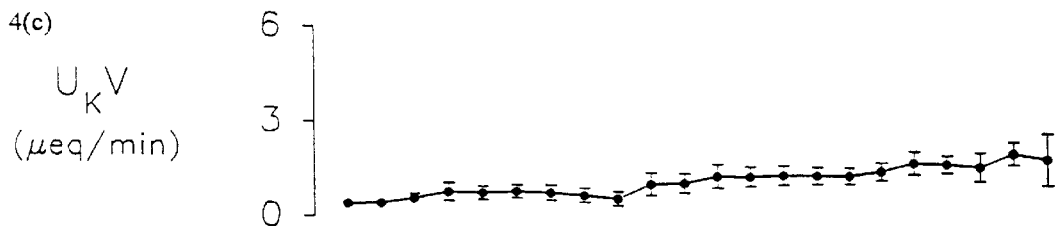
Fig. 4(c) $U_KV$ (μeq/min)
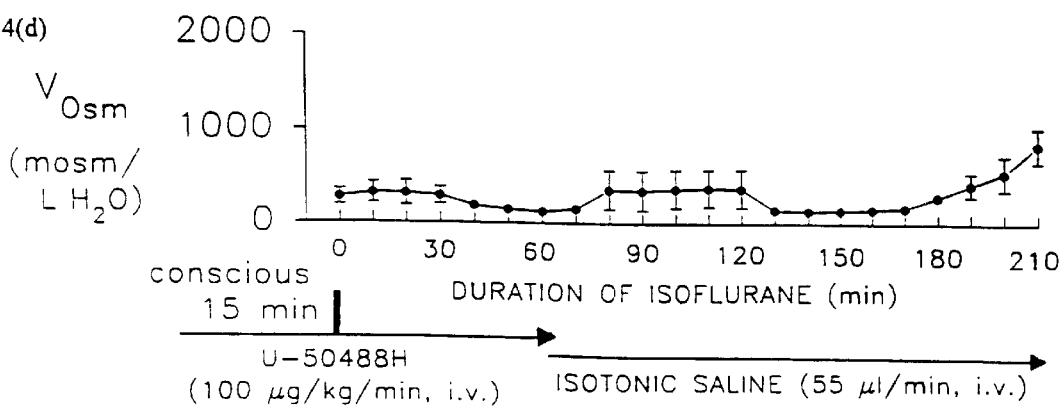
Fig. 4(d) $V_{Osm}$ (mosm/L $H_2O$)
conscious 15 min
U-50488H (100 μg/kg/min, i.v.)
DURATION OF ISOFLURANE (min)
ISOTONIC SALINE (55 μl/min, i.v.)

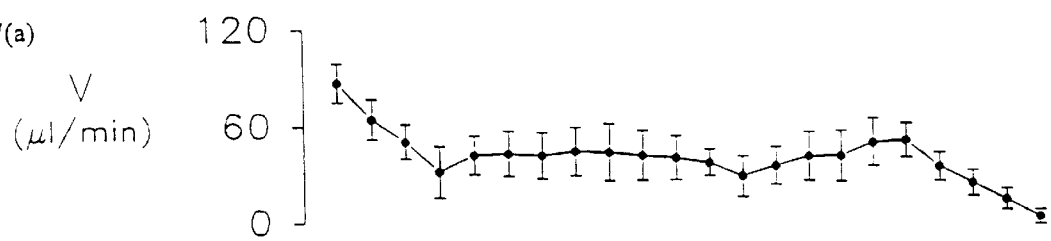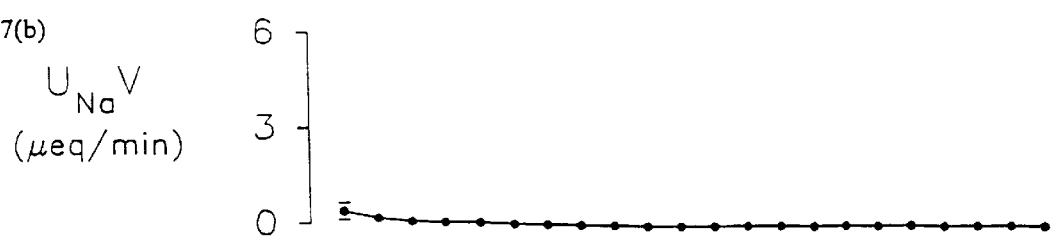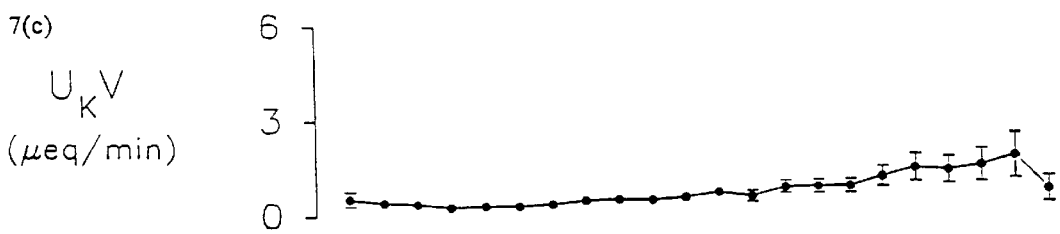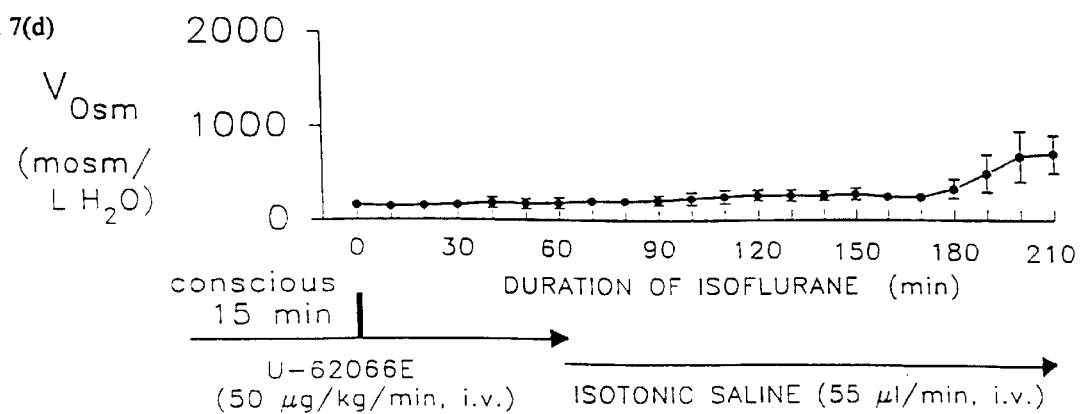

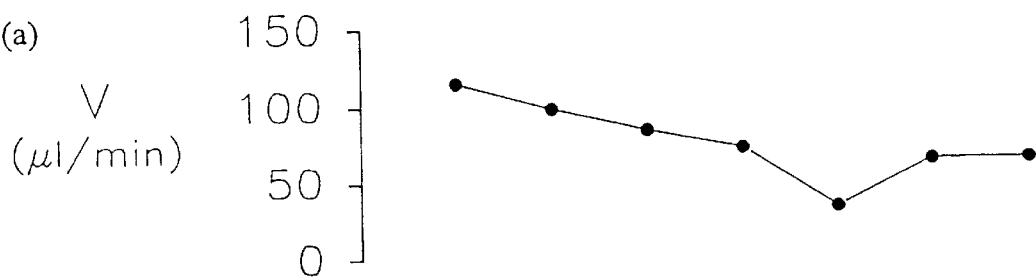
Fig. 8(a) V (μl/min)
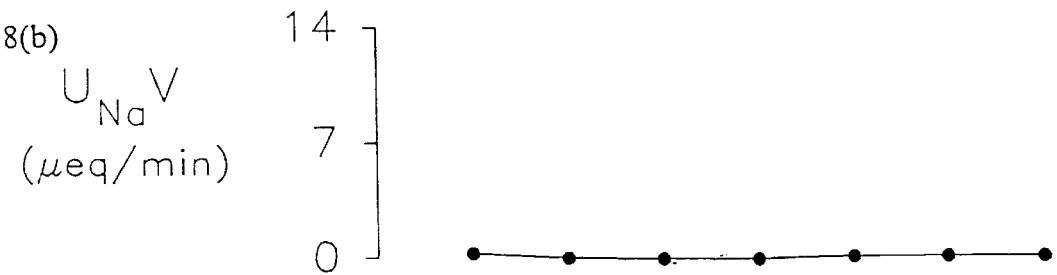
Fig. 8(b) $U_{Na}V$ (μeq/min)
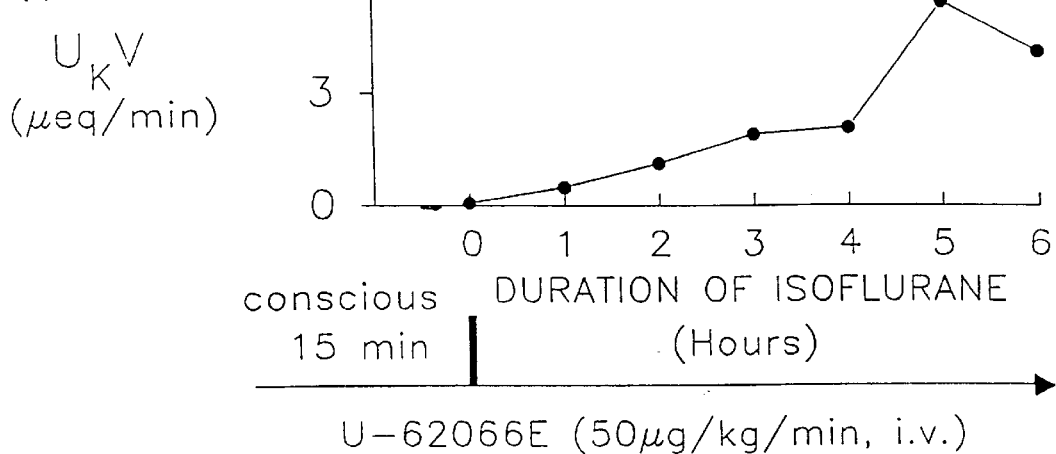
Fig. 8(c) $U_KV$ (μeq/min)
conscious 15 min    DURATION OF ISOFLURANE (Hours)
U-62066E (50μg/kg/min, i.v.)

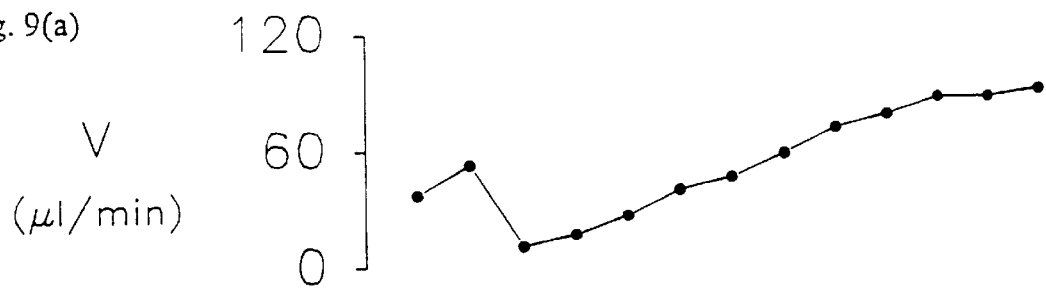
Fig. 9(a) V (μl/min)
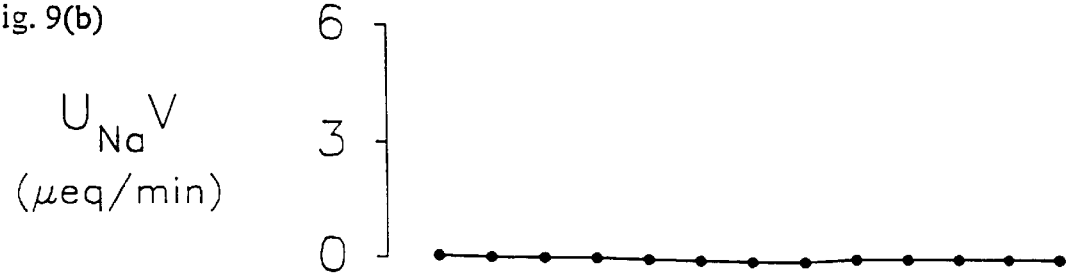
Fig. 9(b) $U_{Na}V$ (μeq/min)
Fig. 9(c) $U_KV$ (μeq/min)
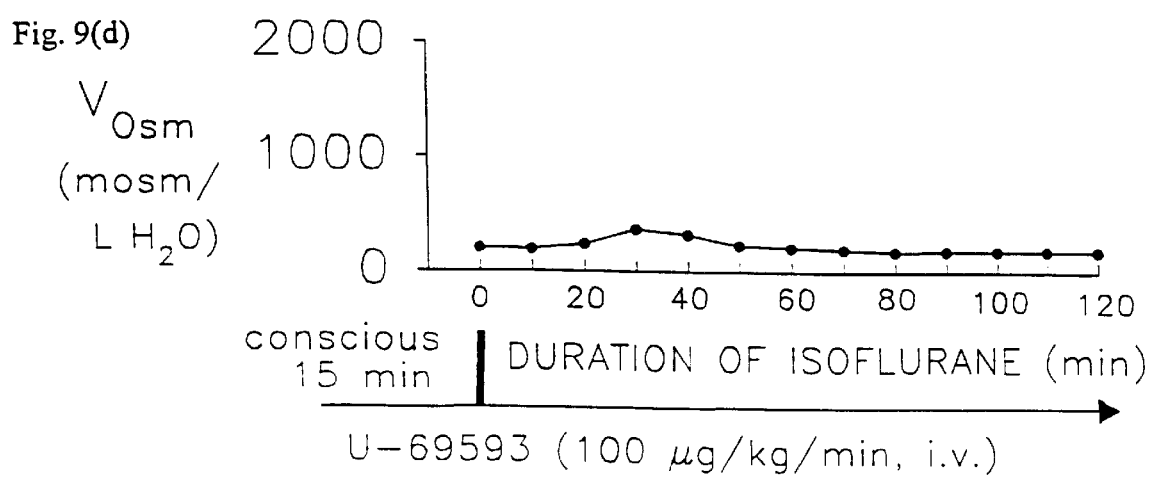
Fig. 9(d) $V_{Osm}$ (mosm/L H$_2$O)
conscious 15 min | DURATION OF ISOFLURANE (min)
U-69593 (100 μg/kg/min, i.v.)

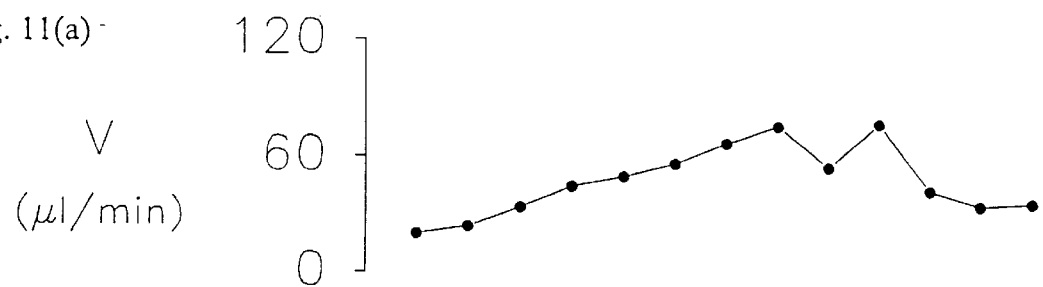
Fig. 11(a) V (μl/min)
Fig. 11(b) $U_{Na}V$ (μeq/min)
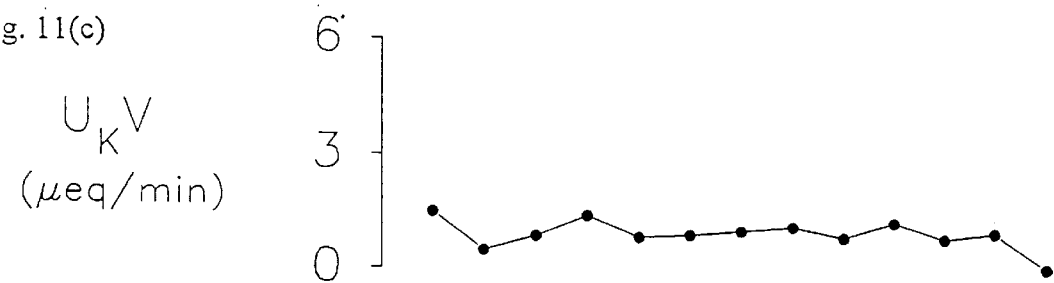
Fig. 11(c) $U_K V$ (μeq/min)
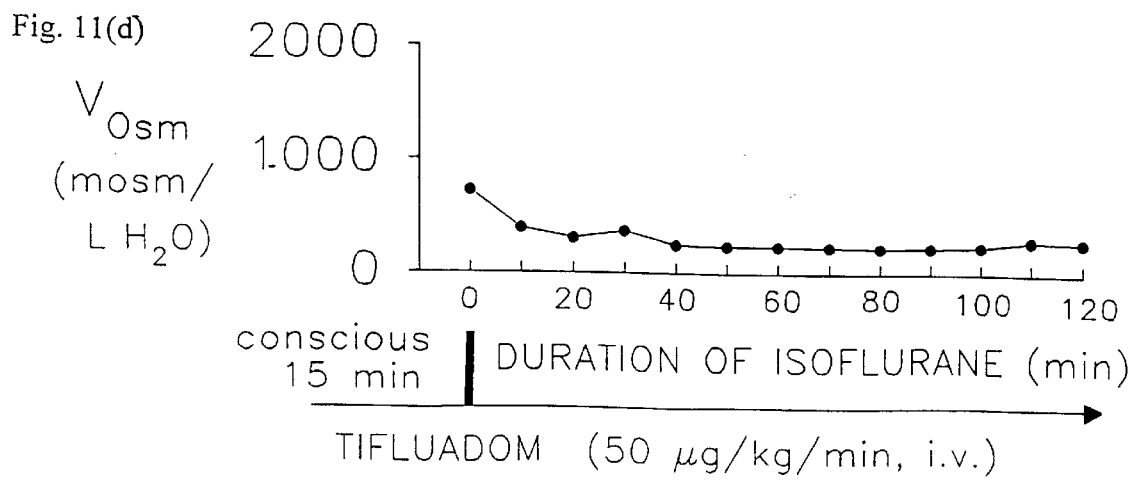
Fig. 11(d) $V_{Osm}$ (mosm/L $H_2O$)
conscious 15 min | DURATION OF ISOFLURANE (min)
TIFLUADOM (50 μg/kg/min, i.v.)

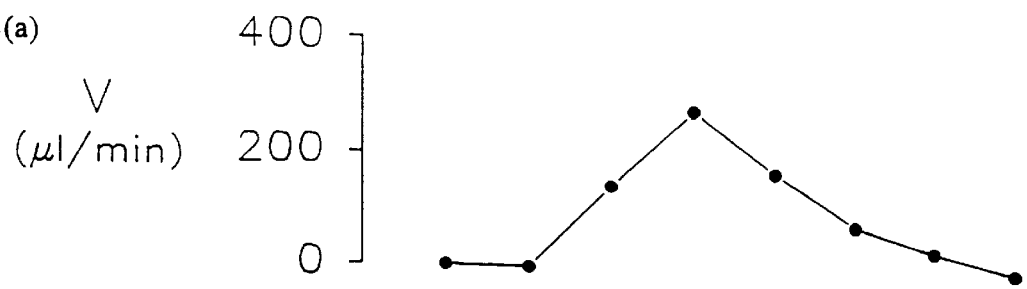
Fig. 13(a) V (μl/min)
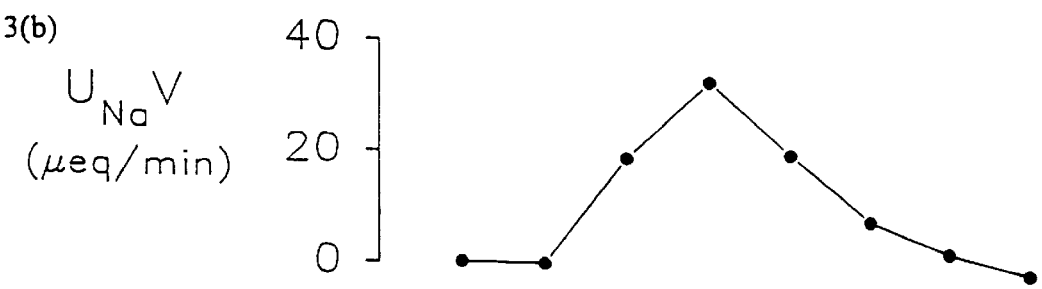
Fig. 13(b) $U_{Na}V$ (μeq/min)
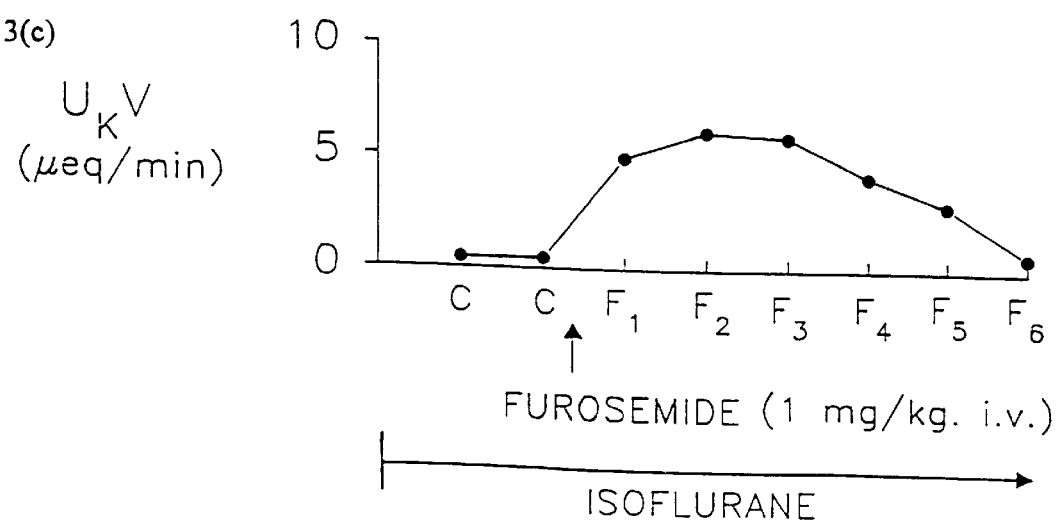
Fig. 13(c) $U_{K}V$ (μeq/min)
FUROSEMIDE (1 mg/kg. i.v.)
ISOFLURANE

METHOD FOR MAINTAINING KIDNEY FUNCTION DURING SURGERY OR SEVERE TRAUMA UNDER GENERAL ANESTHESIA

The benefit of the Jun. 11, 1996 filing date of provisional application Ser. No. 60/040,272 is claimed under 35 U.S.C. § 119(e).

This invention pertains to diuretics, particularly to diuretics that are used during surgery or severe trauma under general anesthesia.

During surgery or severe trauma, gaseous (volatile) general anesthetics such as isoflurane, enflurane, desflurane, nitrous oxide, halothane, ethylene, cyclopropane, sevoflurane and methoxyflurane cause an undesirable side effect on the kidneys: the use of gaseous general anesthetics during the stress of surgery or severe trauma causes acute renal failure and the nearly complete shutdown of urine production. There are profound and sustained reductions in urine output (antidiuresis), urinary sodium excretion (antinatriuresis), and urinary potassium excretion (antikaluresis). When renal function is thus impaired, the kidneys do not produce normal amounts of urine. Water then accumulates in the vascular and interstitial compartments of the body, leading to fluid overload and electrolyte imbalance. In a healthy surgical patient with normal cardiovascular function, the fluid retention and electrolyte imbalance do not necessarily present complications. But potentially life-threatening complications can develop if the same amount of fluid is retained, or if the same electrolyte imbalance occurs in a surgical patient with a preexisting cardiovascular or renal condition, such as hypertension, angina, hepatic cirrhosis, congestive heart failure, renal failure, myocardial infarction, or arrhythmia. Potentially life-threatening conditions that can develop during or after surgery under general anesthesia include pulmonary edema, seizures, angina, myocardial infarction, cardiac arrhythmia, heart failure, renal failure, renal tubular necrosis, sepsis, gastrointestinal hemorrhage, and central nervous system edema or dysfunction.

Drugs that function as diuretics in conscious patients often do not function at all, or do not function in the same manner, when used during general anesthesia. There are a few drugs that have been used to increase urine output and to try to protect the kidneys from damage during anesthesia and surgery, but the existing drugs have complications. Drugs that have been used as diuretics during major operations and treatments for severe trauma include the following: high ceiling loop diuretics such as furosemide, bumetanide, and ethacrynic acid; mannitol, an osmotic diuretic; dopamine, a dopaminergic agonist; and clonidine, an alpha-2 adrenoceptor agonist. These drugs have significant limitations in that either they have a limited ability to increase urine output during anesthesia and surgery, or they cause excessive loss of water and electrolytes. Moreover, in surgical patients with a reduced kidney perfusion pressure (e.g. patients with a preexisting renal disease, or patients suffering from shock or hypotension), these drugs are largely ineffective as diuretics. In cases where these agents do produce a diuretic response during anesthesia and surgery, the level of water output can be exceedingly high. In addition, these agents can cause adverse, potentially life-threatening electrolyte imbalances such as hyponatremia (low plasma sodium) or hyperkalemia (high plasma potassium). Disturbances of electrolyte concentration during the peri- or post-operative periods can severely impair cerebral, neuromuscular, respiratory, and cardiac function. The likelihood that an electrolyte imbalance will cause cardiovascular and renal complications greatly increases in elderly patients, patients with a reduced cardiovascular or renal reserve, and patients being treated with certain other drugs such as cardiac glycosides, corticosteroids, amphotericin B, or other diuretics.

Furosemide, bumetanide and ethacrynic acid are short acting loop diuretics (none of which are opioid agonists). Furosemide is currently one of the drugs most frequently selected for increasing urine output during surgery under general anesthesia. Furosemide has been used to treat fluid overload and hypertension in the following settings: (1) following renal transplant, (2) as an adjunct in reducing intracranial pressure in patients undergoing surgery for intracranial hematomas, (3) for the treatment of edema associated with renal failure, and (4) as an adjunct in treating acute pulmonary edema. Furosemide is administered during a surgical procedure, but not before. Adverse effects related to fluid or electrolyte disturbances can include hyperglycemia, hyperuricemia, hypokalemia, hyponatremia, hypovolemia, hypochloremic alkalosis, tachycardia, oliguria (diminished output of urine), and arrhythmias. Furosemide can also cause acute hypotensive episodes during rapid diuresis that can then lead to further impairment of renal function. Moreover, furosemide can cause excessive losses of water, sodium, potassium, and calcium that can lead to life-threatening complications as severe as those caused by renal shutdown. For example, the marked rise in urine output caused by furosemide can cause renal failure by inducing hypovolemia (abnormally decreased volume of circulating blood). Hypovolemia is a particular problem in patients who are only minimally euvolemic (normal blood volume).

Y. Hamaya et al., "Diuretic Effect of Clonidine during Isoflurane, Nitrous Oxide, and Oxygen Anesthesia," Anesthesiology, vol. 81, pp. 811–819 (1994) discussed the diuretic effect of clonidine (not an opioid agonist) during general anesthesia and surgery in human patients. When clonidine was administered 90 minutes before anesthesia it caused significant diuresis during surgery, but also produced substantial losses of sodium and potassium. Clonidine also produced a substantial decrease in mean arterial pressure and heart rate in these patients. Further, clonidine can alter the pharmacological action of other drugs that are frequently co-administered during various surgical operations. For example, the heart rate response to intravenous administration of atropine is attenuated. Moreover, the pressor response to intravenous ephedrine is augmented by clonidine pretreatment.

Mannitol (not an opioid agonist) is extensively employed as an osmotic diuretic. Mannitol is sometimes used to decrease intracranial pressure and fluid volume. Mannitol has also been used for prophylaxis and the treatment of acute renal failure during cardiovascular operations and in treating severe traumatic injury. However, mannitol causes extracellular (e.g., intravascular and interstitial) volume expansion, and it can precipitate congestive heart failure and pulmonary edema in patients with limited cardiac reserve. Mannitol can cause other major adverse reactions including hypernatremia, hyperkalemia, hyperosmolality, circulatory overload, renal failure, allergic reactions, and seizures. Mannitol's effects on plasma potassium and sodium can produce potentially life-threatening complications in surgical patients with underlying conditions such as cardiac or renal disease, or in patients with preexisting electrolyte abnormalities.

Dopamine is an inotropic agent that stimulates dopaminergic and alpha-adrenergic receptors. Dopamine is sometimes used in surgical settings to improve renal blood flow in an attempt to augment urine flow. Dopamine is also a natriuretic agent; it produces an increase in urine sodium excretion. Adverse effects of dopamine infusion in surgical patients can include hypotension, hypertension, tachycardia, hyponatremia, and cardiac arrhythmias. Dopamine can also cause renal artery vasoconstriction, thereby reducing urinary sodium and water excretion. Dopamine is contraindicated in patients receiving cyclopropane or halothane anesthesia.

There is a continuing, unfilled need for improved diuretic compounds that may be used during surgery or treatment for severe trauma under a general, gaseous anesthetic. There is particularly an unfilled need for diuretic compounds that induce a constant level of urine flow, that protect the kidneys from damage, and that do not cause excessive loss of water or electrolytes. I.e., there is a continuing, unfilled need for diuretic compounds that preserve kidney function while maintaining homeostasis of intravascular volume, electrolyte concentration, and osmolality.

Endogenous opioid receptors have been identified in both the central nervous system (brain and spinal cord), and in the periphery. These receptors have been classified into three major subtypes: mu, delta, and kappa receptors. Morphine and related compounds are often called "mu opioids," because they bind to mu receptors. The so-called "kappa opioid agonists," first discovered about fifteen years ago, bind instead to kappa receptors with high selectivity. A compound is considered a kappa opioid agonist if it binds to kappa receptors in a binding assay, or if it demonstrates kappa agonist activity in functional assays. The kappa agonists are as effective as morphine in relieving pain. But unlike morphine, kappa agonists are not addictive, and do not cause cardiovascular or respiratory depression at the doses required for analgesia.

The kappa opioids, which are unique in being analgesic without being addictive, were initially regarded as a potential breakthrough in the therapeutic management of chronic pain. However, despite substantial research efforts by several pharmaceutical companies over the past fifteen years, no kappa opioid agonists have been approved in any country for any indication to date. The reason is that kappa agonists cause dysphoria that is not well tolerated by patients during chronic use. The sensation of dysphoria differs between individuals, variously including dizziness, fatigue, paresthesia, headache, feeling "high," thinking abnormally, emotional lability, facial flushing, nausea, and vomiting. Unsuccessful attempts have been made to separate the analgesic and dysphoric properties of kappa agonists.

Early studies of the analgesic effects of kappa opioids recognized a side effect of those compounds, namely that they produced a marked diuretic response in conscious laboratory animals (i.e., they increase urine output). It was also observed that kappa opioids have antinatriuretic properties in conscious laboratory animals (i.e., they cause sodium retention). The diuretic and antinatriuretic properties of kappa opioids have not been the focus of much research because of the dysphoria induced by these compounds. The induced dysphoria effectively precludes any chronic use of a kappa opioid.

Each of the following patents discloses that kappa opioid agonists have various characteristics including diuretic properties: Horwell et al., U.S. Pat. Nos. 4,663,343, 4,906,655, 4,965,278, 5,019,588, 5,063,242; Clemence et al., U.S. Pat. Nos. 4,888,355, 4,988,727; Zimmerman et al., U.S. Pat. Nos. 4,891,379, 4,992,450, 5,064,834, 5,319,087, 5,422,356; Naylor et al., U.S. Pat. No. 5,116,842; Moura et al., U.S. Pat. Nos. 5,068,244, 5,130,329; and McKnight et al., U.S. Pat. Nos. 5,317,028, and 5,369,105.

S. Salas et al., "[N-Methyl-Tyr$^1$,N-Methyl-Arg$^7$-D-Leu$^8$]-Dynorphin-A-(1–8) Ethylamide, a Stable Dynorphin Analog, Produces Diuresis by Kappa-Opiate Receptor Activation in the Rat," J. Pharmacol. Exp. Ther., vol. 262, pp. 979–986 (1992) reported a series of experiments on the effect of E-2078, a kappa opioid agonist, on urine flow in rats. In these experiments, conscious rats were reported to have a basal urine flow rate of 40±7.5 $\mu$l/min. After i.v. administration of 50 $\mu$g of E-2078, the urine flow rate in the conscious rats increased to 118±22 $\mu$l/min after 15–30 minutes, an increase of 78 $\mu$l/min over the baseline flow rate. When the study was repeated in rats anesthetized with pentobarbital, a barbiturate (not a gaseous anesthetic), the basal urine flow rate dropped substantially, to 4.0±0.5 $\mu$l/min. When 50 $\mu$g of E-2078 was administered i.v. to the anesthetized rats, the urine flow rate increased, but only slightly, to 6.3±1.0 $\mu$l/min, still well below the basal rate in the conscious animals. Pentobarbital anesthesia dramatically reduced the ability of the kappa agonist to increase urine output. The intravenous (i.v.) administration of 50 $\mu$g E-2078 was also reported to decrease urinary sodium excretion from 3.0±0.6 $\mu$Eq/min (basal) to 1.4±0.4 $\mu$Eq/min (at 30–45 min) in conscious rats. In pentobarbital-anesthetized rats, basal urinary sodium excretion was reported to drop to 0.2 $\mu$Eq/min. However, the i.v. administration of 50 $\mu$g of E-2078 to the pentobarbital-anesthetized rats did not evoke an antinatriuretic response, but instead caused a slight increase in urinary sodium excretion to 0.3±0.1 $\mu$Eq/min.

In these experiments of Salas et al., as well as in the reported work of others discussed below, the animals were anesthetized with a barbiturate, and not with an inhaled gaseous anesthetic such as isoflurane, halothane, or nitrous oxide. These two classes of anesthetic agents (barbiturates and gaseous anesthetics) have very different physiological properties. Effects produced by one type of anesthetic cannot be extrapolated to the other. In contemporary surgical practice in humans, barbiturates are used only as presurgical anxiolytic agents or as induction agents, and are not used for maintaining anesthesia during surgery. Gaseous anesthetics are used to maintain anesthesia in humans during surgery.

Barbiturates modulate the action of neurotransmitters at specific receptor sites. For example, it is known that barbiturates bind to γ-aminobutyric acid (GABA) receptors, thereby enhancing the inhibitory action of GABA on the central nervous system. By contrast, gaseous anesthetics do not directly bind to specific receptor sites. Instead, gaseous anesthetics act on the lipid matrix of the cell membrane to distort the channels involved in sodium conductance, thereby stabilizing nerve membranes and reducing nerve activity.

Barbiturates are metabolized by liver enzymes to active metabolites. Gaseous anesthetics are eliminated, largely unchanged, through expiration. Barbiturates and gaseous anesthetics have different effects on the release of circulating hormones (e.g., epinephrine, histamine, angiotensin II, vasopressin, aldosterone, adrenocorticotropic hormone). Barbiturates increase renal vascular resistance, while gaseous anesthetics decrease renal vascular resistance. Barbiturates cause central nervous system stimulation and can induce seizures, whereas gaseous anesthetics do not cause seizure activity.

Because barbiturates and gaseous anesthetic agents operate through separate mechanisms, have different effects on neural and hormonal systems, and produce different central and peripheral nervous system responses, results obtained with one type of anesthetic cannot be extrapolated to the other. In particular, barbiturates and gaseous anesthetics use different mechanisms to produce acute renal failure and to decrease urine and electrolyte output during surgery. The same physiological result (e.g. impaired renal function during anesthesia and surgery) therefore does not imply the same cause, nor does it imply a similar mode of treatment.

G. Slizgi et al., "Effects of the Highly Selective Kappa Opioid, U-50,488, on Renal Function in the Anesthetized Dog," J. Pharmacol. Exp. Ther., vol. 230, pp. 641–645 (1984) reported a series of experiments on U-50,488-induced diuresis in dogs. Dogs were anesthetized with sodium pentobarbital, and were administered 0.9% saline at a rate of 0.2 ml/min/kg. Groups of anesthetized dogs were given a single i.v. dose of U-50,488, at one of the following dosages: 0.2, 1, or 5 mg/kg. Despite the high saline infusion rate (0.2 ml/min/kg), control urine flow rates in these groups of dogs before U-50,488 administration only ranged from 0.031±0.007 (in the lowest dose group, 0.2 mg/kg) to 0.063±0.020 ml/min/kg (in the middle dose group, 1 mg/kg). The administration of U-50,488 caused a dose-dependent increase in urine flow rate, peaking within two hours. The lowest dose (0.2 mg/kg) produced about a 2.5-fold increase in urine flow rate (i.e. to approximately 0.078 ml/min/kg). The highest dose (5 mg/kg) produced about a 7-fold increase in urine flow rate (from 0.047 ml/min/kg, estimated basal level from average of range, to approximately 0.329 ml/min/kg). Heroic intravenous doses (e.g. 0.2, 1 and 5 mg/kg) of U-50,488H—doses that would never be administered to a human—were necessary to produce these responses in the pentobarbital-anesthetized dogs. That these doses were excessive is illustrated, for example, by G. Peters et al., "Diuretic Actions in Man of a Selective Kappa Opioid Agonist: U-62,066E," J. Pharmacol. Exp. Ther., vol. 240, pp. 128–131 (1987). Peters et al. reported that in conscious humans the intramuscular administration of only 5 $\mu$g/kg of the kappa agonist spiradoline (U-62,066E) (which is about twice as potent a diuretic as U-50,488H) evoked a pronounced diuretic response. See also G. Rimoy et al., "The Cardiovascular and Central Nervous System Effects in the Human of U-62,066E," Eur. J. Clin. Pharmacol, vol. 46, pp. 203–207 (1994), reporting that a 3.2 $\mu$g/kg dose of spiradoline caused sedation, significant dysphoria, and no significant euphoria in humans.

D. Brooks et al., "Opiate Receptors in the Blood-Brain Barrier Mediate Kappa Agonist-Induced Water Diuresis," J. Pharmacol. Exp. Ther., vol. 266, pp. 164–171 (1993) reported experiments suggesting that the ability to cross the blood-brain barrier may be important in kappa opioid-induced water diuresis. The underlying motivation was presumably that if kappa opioids could be shown to produce a diuretic response by action solely in the periphery (i.e., by action outside the brain), then new generation kappa opioids that did not enter the brain might be found useful in treating chronic conditions without the complications of central nervous system effects such as analgesia and dysphoria. For example, if new generation kappa agonists could be developed that did not have analgesic/dysphoric properties, but that could still produce a diuretic response, the compounds might be useful as water diuretics for chronic hyponatremic disorders. Conscious rats were infused intravenously with saline at 10 $\mu$l/min, and were hydrated by a bolus administration of lukewarm water intragastrically. The effects of kappa opioids on the rats were then studied. When urinary output exceeded the infusion rate by 2 ml, it was replaced by lukewarm tap water via the stomach catheter. Two kappa opioids that cross the blood-brain barrier, and one that does not, were all shown to produce a dose-dependent increase in urine output in conscious rats. The effects of the same kappa opioids were also examined in conscious dogs that were infused intravenously with 0.45% saline containing 2.5% dextrose at 0.05 ml/kg/min. In the conscious dogs, none of the kappa opioids produced a change in urine output, although some central nervous system side effects (e.g., trembling, restlessness) were observed with the kappa opioids that enter the brain. When these studies were repeated in dogs that were lightly anesthetized with pentobarbital, only the kappa opioids that cross the blood-brain barrier produced a diuretic response. Because the peripherally-acting kappa opioid (i.e., the kappa opioid that does not cross the blood-brain barrier) produced a diuretic response in conscious rats, but not in conscious dogs, it was concluded that kappa opioids have different peripheral mechanisms for producing diuretic responses (e.g., different direct actions on the kidneys) in rats and dogs. Conscious humans are probably more similar to dogs in this regard (the peripheral mechanisms that control urine output). The authors thus concluded that it was unlikely that a peripherally-acting, kappa-agonist water diuretic with limited effects on the central nervous system could be successfully developed for chronic use in humans. To the inventor's knowledge, no such compounds have in fact been developed to date.

In the studies of both Brooks et al. and Slizgi et al., dogs were anesthetized with pentobarbital, which is a barbiturate. As previously discussed, it cannot be inferred that drugs will produce the same responses under conditions of barbiturate anesthesia and gaseous anesthesia, because the two types of anesthetics evoke different physiological responses acting through different mechanisms. Furthermore, the barbiturate pentobarbital is not used in humans to maintain anesthesia during surgery. In the Brooks et al. investigation, dogs were not studied during surgery under general anesthesia. Rather, the dogs were surgically implanted with arterial catheters under anesthesia, and were then allowed three weeks to recover. On the day of the experiments, the effects of kappa opioids were examined in pentobarbital-anesthetized dogs that did not undergo any major invasive surgical operation. The absence of any invasive surgery during the general anesthesia is significant, as it is recognized that it is the combination of anesthesia and the surgical insult that causes impairment of renal function and reduced urine and electrolyte output. See D. R. Bevan et al., "Renal Function During and After Anaesthesia and Surgery: Significance for Water and Electrolyte Management," Brit. J. Anaesth., vol. 45, pp. 968–975 (1973). By contrast, Slizgi et al. studied the renal effects of kappa opioids on pentobarbital-anesthetized dogs on which invasive surgery was performed. Observed urine flow rates were low (as compared to the rates of intravenous saline infusion), and only heroic doses of the kappa agonist were found to produce a significant increase in urine flow rate.

D. Kapusta, "Opioid Mechanisms Controlling Renal Function," Clin. Exp. Pharmacol. Physiol. vol. 22, pp. 891–902 (1995) gives a review of the effect of opioids on renal function.

N. Ashton, "κ-Opioid-Receptor Agonists Modulate the Renal Excretion of Water and Electrolytes in Anaesthetized Rats," Br. J. Pharmacol., vol. 99, pp. 181–185 (1990), reported experiments in which rats anesthetized with Inactin (a barbiturate that is not used for maintenance of anesthesia in humans) were loaded intravenously with hypotonic saline at a very high infusion rate (150 $\mu$l/min) for three hours. (This water-loading presumably produced non-physiological conditions in the animals). After three hours of the hypotonic saline loading, the rats received a subcutaneous injection of U-50,488 or tifluadom (a kappa opioid), at the high doses of 10 and 3.5 mg/kg, respectively. Urinary flow for rats given U-50,488 increased from a baseline rate of about 150 μl/min (about equal to the rate of the hypotonic saline infusion), to a peak of about 220 μl/min at 60 minutes after injection. The increased urine flow was not sustained, however, and urine flow dropped below baseline to about 90 μl/min at 200 minutes after injection. Tifluadom produced a similar diuresis.

P. Reece et al., "Diuretic Effects, Pharmacokinetics, and Safety of a New Centrally Acting Kappa-Opioid Agonist (CI-977) in Humans," J. Clin. Pharmacol., vol. 34, pp. 1126–1132 (1994) reported that the intramuscular administration of CI-977, a kappa opioid agonist, increased urine flow in conscious humans. However, negative side effects were reported, including dizziness, fatigue, paresthesia, headache, vasodilation (facial flushing), emotional lability, feeling "high," and abnormal thinking. The dose of CI-977 ranged from 5 to 25 μg in individuals weighing from 50.5 to 117.9 kg. Reece et al. reported that the diuresis produced by kappa receptor agonists may be mediated by alterations in antidiuretic hormone activity.

G. Peters et al., "Diuretic Actions in Man of a Selective Kappa Opioid Agonist: U-62,066E," J. Pharmacol. Exp. Ther., vol. 240, pp. 128–131 (1987), disclosed that the kappa agonist U-62,066E injected intramuscularly at doses ranging from 2 to 6 μg/kg induced water diuresis in conscious humans, without increases in sodium, potassium, or chloride excretion.

In conscious rats, administration (i.v. bolus or infusion) of kappa opioids produces changes in urine flow similar to those produced by other clinically used diuretics. For example, D. Kapusta et al., "Role of Renal Nerves in Excretory Responses to Administration of Kappa Agonists in Conscious Spontaneously Hypertensive Rats," J. Pharmacol. Exp. Ther., vol. 251, pp. 230–237 (1989) reported that in conscious rats intravenous infusion of the kappa opioid U-50,488H (20 μg/kg/min) produced a diuretic response that was rapid in onset (10 minutes), of large magnitude (150–200 μl/min increase over baseline, with a peak magnitude at 30–40 minutes) and of relatively short duration (approximately 60–80 minutes).

D. Kapusta et al., "Central Kappa Opioid Receptor-Evoked Changes in Renal Function in Conscious Rats: Participation of the Renal Nerves," J. Pharmacol. Exp. Ther., vol. 267, pp. 197–204 (1993) reported that in conscious rats administration of U-50,488H into the lateral ventricle of the brain produced a diuretic response that was similar in magnitude and time course to those observed in the other studies reported above. See also D. Kapusta et al., "Central Kappa Opioids Blunt the Renal Excretory Responses to Volume Expansion by a Renal Nerve-Dependent Mechanism," J. Pharmacol. Exp. Ther., vol. 273, pp. 199–205 (1995).

G. Rimoy et al., "Mechanism of diuretic action of spiradoline (U-62,066E)—a Kappa Opioid Receptor Agonist in the Human," Br. J. Clin. Pharmac., vol. 32, pp. 611–615 (1991) reported that the kappa agonist U-62,066E significantly increased urine output and decreased urine osmolality in conscious healthy humans. It was reported that U-62,066E altered neither plasma antidiuretic hormone activity nor renal hemodynamics. Rimoy et al. concluded that a mechanism other than a change in antidiuretic hormone activity or renal hemodynamics was responsible for producing kappa opioid-induced diuretic effects in conscious humans.

It has unexpectedly been discovered that kappa-opioid agonists may be used to prevent the impairment of renal function that occurs during surgery or treatment of severe trauma under gaseous anesthesia. Not only do kappa opioid agonists preserve renal function and maintain a constant level of urine output during anesthesia and surgery, but they also preserve sodium, potassium, calcium, and total osmolality, thereby helping to keep plasma electrolyte levels constant.

The preservation of urine flow while maintaining body sodium, potassium, calcium, and total osmolality levels during surgery or treatment of severe trauma under gaseous anesthesia has never previously been achieved. Kappa agonists may be used in healthy patients, but are particularly useful for surgical patients with compromised cardiovascular or renal function, or otherwise having a prior condition of water or electrolyte imbalance. This invention encompasses the use of kappa opioid agonists to induce diuresis in anesthetized mammals (including humans) during surgery or treatment of severe trauma, where the anesthesia is induced by a volatile, inhaled anesthetic, including one or more of the following: isoflurane, enflurane, desflurane, nitrous oxide, halothane, ethylene, cyclopropane, sevoflurane, and methoxyflurane.

To the inventor's knowledge, no prior reference has suggested a method for maintaining a constant and adequate output of urine while maintaining homeostasis of blood volume, electrolyte concentration, and osmolality during gaseous anesthesia and surgery or trauma. All known prior diuretic agents that have been used during surgery (e.g., furosemide, ethacrynic acid, mannitol) are known to have significant limitations. For example, after the initial drop in urine flow induced by anesthesia and surgery, the administration of current, clinically-used diuretics evokes a characteristic spike increase in urine flow—sometimes to undesirably high levels—followed by a rebound shutdown of urine output. The fluctuations in urine output associated with the use of prior diuretics cause an increase, then a decrease, and then another increase in intravascular volume (i.e., hypervolemia, hypovolemia, and hypervolemia, respectively). Large fluctuations in plasma electrolyte concentration and osmolality often result as well. In addition, prior diuretics can be ineffective in modifying urine output in surgical patients with certain pre-existing conditions (e.g., cirrhosis with ascites, congestive heart failure, or chronic renal failure, or hypotension following severe traumatic injury or shock).

Although it was previously known that kappa opioids produce a diuretic response in conscious animals, it was nevertheless surprising to find that these compounds were effective in controlling the adverse effects of gaseous anesthesia on kidney function during surgery or trauma. The onset, magnitude, and duration of the effects of kappa opioid pretreatment on anesthetized rats during surgery were significantly different from the effects on conscious animals. In addition, the required dose is substantially different in conscious and anesthetized animals. The dose of kappa agonist that produced the maximal diuretic response in a conscious animal did not prevent or reverse the impaired renal function induced by surgery and isoflurane anesthesia. By sheer chance it was discovered that by substantially increasing the dose of a kappa agonist, and by controlling the timing of its administration, a qualitatively different response can be produced during surgery or treatment of severe trauma under gaseous anesthesia. In particular, a four-fold higher dose of kappa agonist than will induce diuresis in a conscious animal was found to be effective in completely preventing the surgery and gaseous anesthetic-induced impairment of kidney function; it was also found that the kappa agonist was most effective only when administered as a pretreatment while the animal was in conscious state, during a period of time prior to the start of anesthesia and surgery. No prior reference has suggested these effects.

For example, intravenous in fusion (55 μl/min) of conscious rats with 25 μg/kg/min of U-50,488H produced a marked diuresis, but the same dose was completely ineffective as a diuretic in rats during surgery and isoflurane anesthesia. However, when rats were first pretreated with a four-fold larger dose of U-50,488H (100 μg/kg/min) while conscious for 15 minutes, and were then anesthetized (induced with thiopental and maintained with isoflurane) and operated upon, the characteristic changes in urine output caused by kappa agonists in conscious animals did not occur (i.e., there was not a profound diuretic response and then a compensatory antidiuretic response). Instead, urine flow rate remained constant during infusion of U-50,488H (60 minutes) at approximately 50–70 μl/min, a level similar to that observed before administration of anesthesia and surgery. After stopping the infusion of U-50,488H, the urine flow rate remained elevated at a similar level for an additional 100–120 minutes.

These findings are the first to demonstrate a method by which urine output may be preserved during surgery or treatment of severe trauma under gaseous anesthesia without un desirable levels of electrolyte loss. This unique combination of activities is highly desirable during surgery or treatment of severe trauma. Because the action of kappa opioids in maintaining kidney function during surgery appears to be independent of blood pressure, these agents may be particularly useful in surgical patients, and in patients suffering from a severe traumatic injury in which renal perfusion pressure is reduced (e.g., those suffering from shock, hypotension, or renal failure). That the kappa opioids act independent of changes in blood pressure was shown in observations that urine output remained elevated and constant in rats during continuous kappa opioid infusion, despite a reduction in blood pressure to approximately 75–80 mm Hg resulting from long-term isoflurane anesthesia, or resulting from enhancing the level of isoflurane anesthesia. In other observations, it was found that while urine output remained elevated and constant, the reduction in blood pressure resulting from kappa agonist infusion during long-term isoflurane anesthesia was prevented by reducing the inhaled concentration of isoflurane.

Because this novel use for kappa opioid agonists is acute (i.e., for a period of hours) rather than chronic (i.e., for a period of days, weeks, months, or years), the possibility of short-lived dysphoria is an acceptable side effect. P. Reece et al. (1994) reported that the time to onset of adverse effects was normally 15 to 30 minutes post-dose for the kappa opioid CI-977, and that the adverse effects persisted up to 4 hours after intramuscular injection. To prevent the anesthesia-and-surgery-induced impairment of renal function, continuous administration of a kappa agonist preferably begins about 15 to 30 minutes before induction and maintenance of anesthesia and the start of surgery. If the kappa agonist is administered too long before the induction and maintenance of anesthesia (more than about 45–60 minutes before), then an antidiuretic compensatory effect can commence before anesthesia is induced. This compensatory effect can continue during anesthesia, and can block the diuretic effect that the kappa agonist would otherwise exert during anesthesia and surgery.

While a one-time, short-lived dysphoric response to this kappa opioid pretreatment is possible, this potential adverse response is likely to be masked by the actions of other drugs or the anesthetic agent. For instance, drugs such as diazepam (Valium), morphine, meperidine (Demerol), codeine, oxycodone, etc., are typically used as pre-, peri-, and post-operative medications in the surgical patient, and should conceal any dysphoria otherwise resulting from the kappa opioid. By contrast, persistent dysphoric effects make intolerable the chronic administration of kappa opioids for other uses.

BRIEF DESCRIPTIONS OF THE DRAWINGS

Figure 1B:
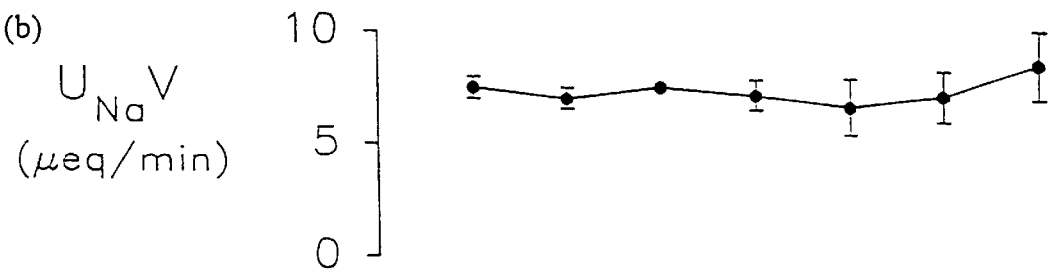
Figure 1C:
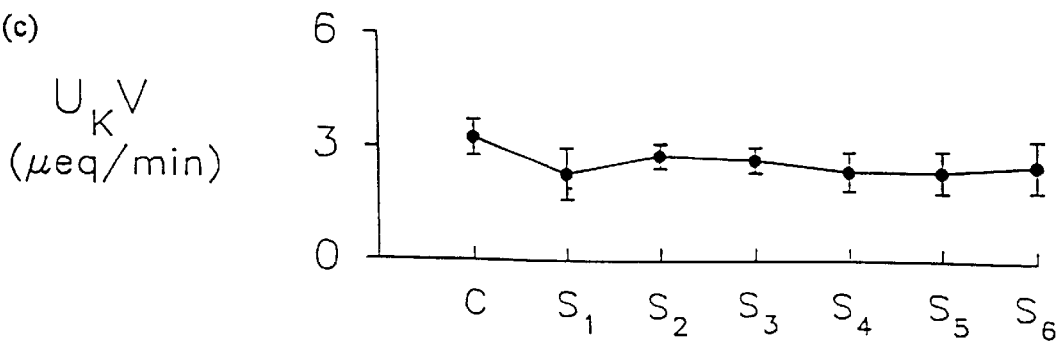
Figure 2A:
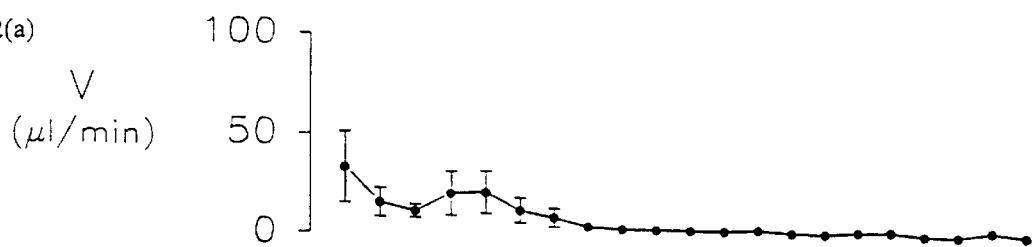
Figure 2B:
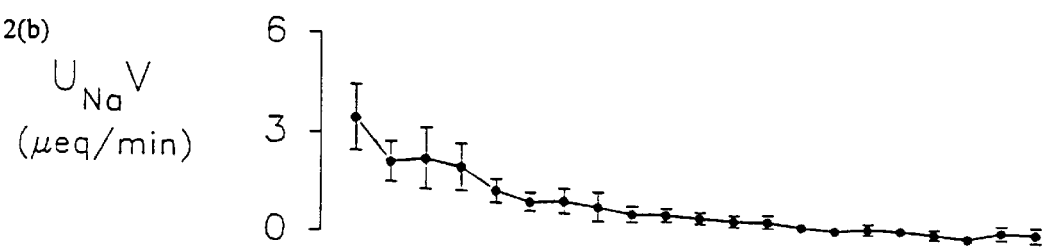
Figure 2C:
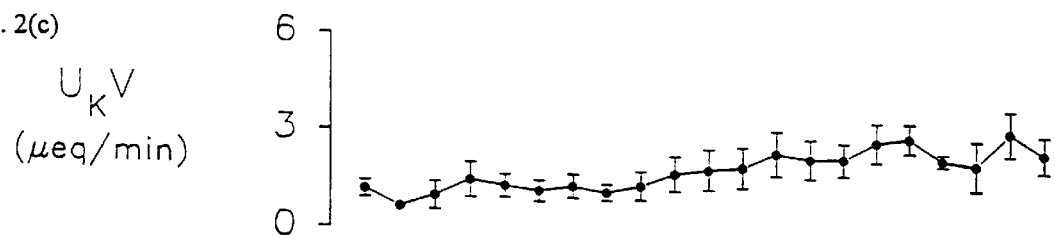
Figure 2D:
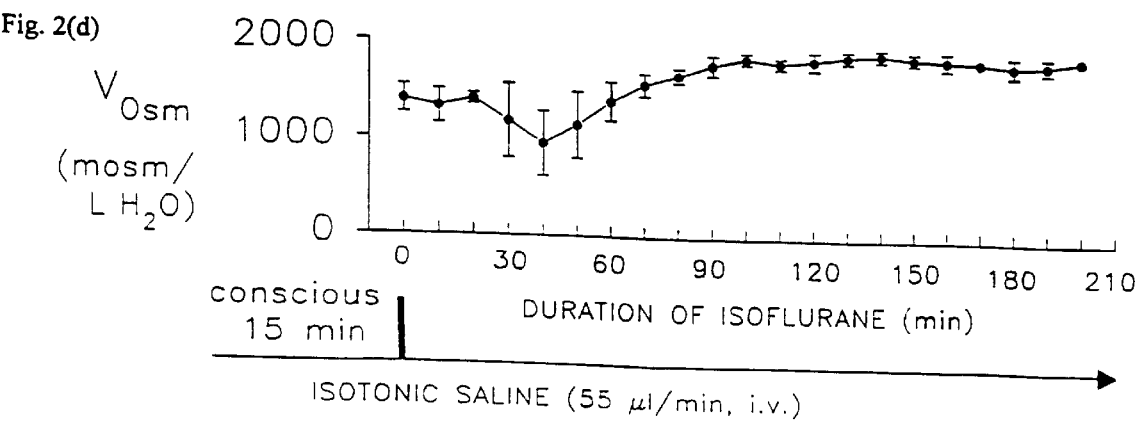

FIGS. 1(a), 1(b), and 1(c) depict the levels of urine flow rate, urinary sodium excretion, and urinary potassium excretion, observed in conscious control rats infused with saline.

FIGS. 2(a)–(d) depict the renal responses of rats upon invasive surgery and isoflurane anesthesia, without any diuretic.

FIGS. 3(a)–(d) illustrate the ability of the kappa opioid agonist U-50,488H to reverse the impairment of urine flow rate produced by the combination of surgery and isoflurane anesthesia.

FIGS. 4(a)–(d) demonstrate the effect of U-50,488H pretreatment on renal response during surgery and isoflurane anesthesia.

Figure 5A:
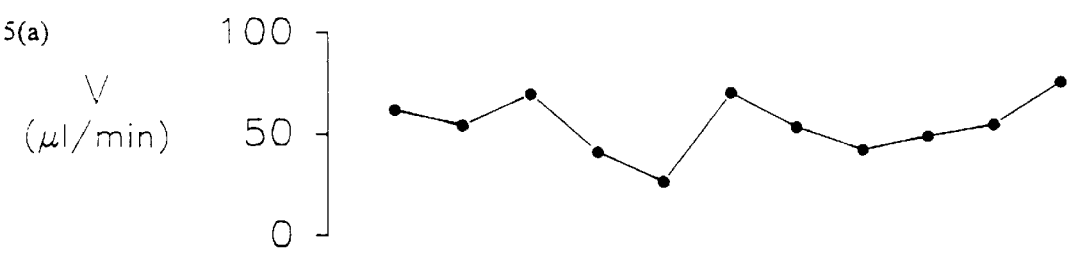
Figure 5B:
Figure 5C:
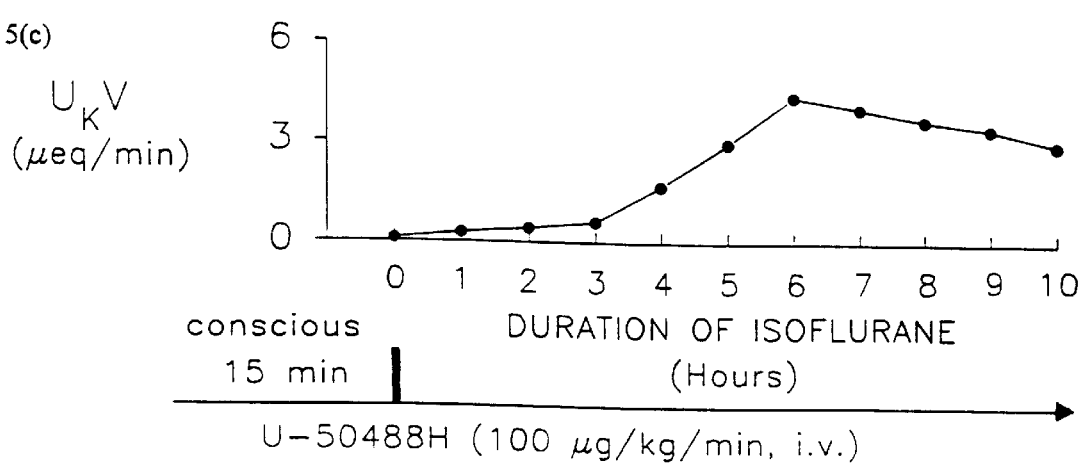
Figure 6A:
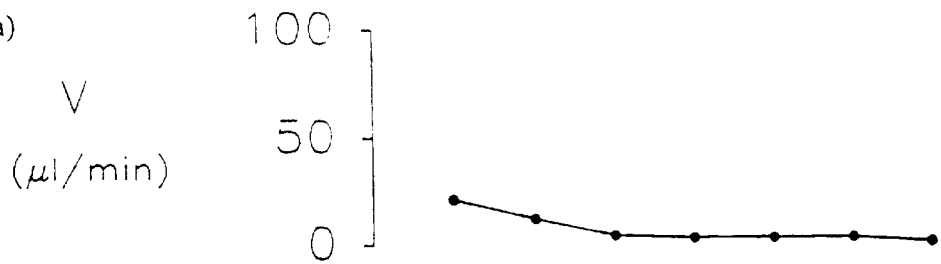
Figure 6B:
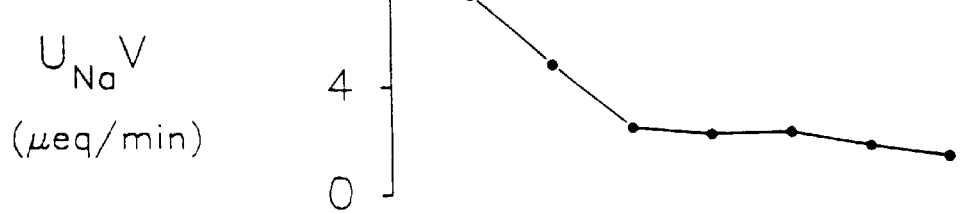
Figure 6C:
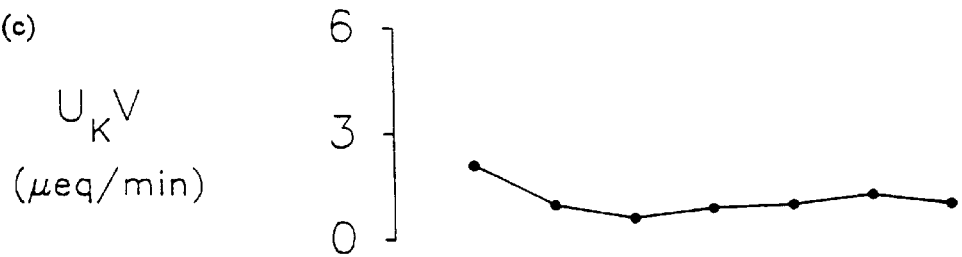
Figure 6D:
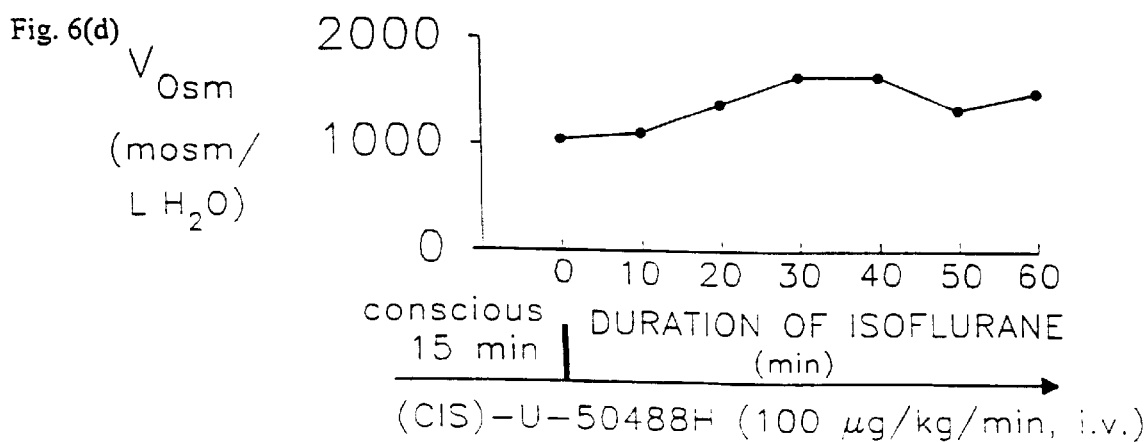
Figure 10A:
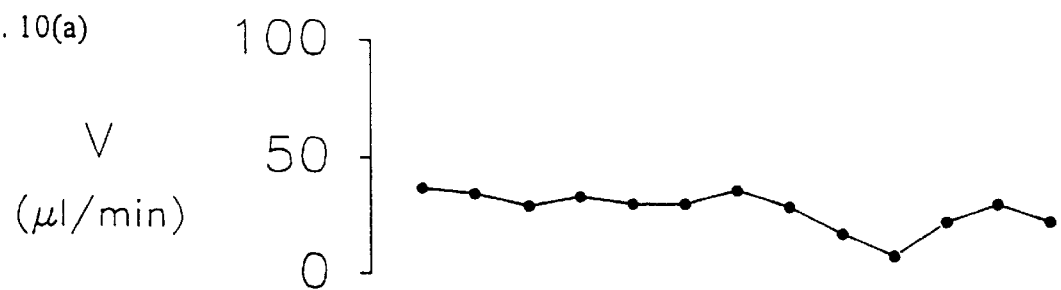
Figure 10B:
Figure 10C:
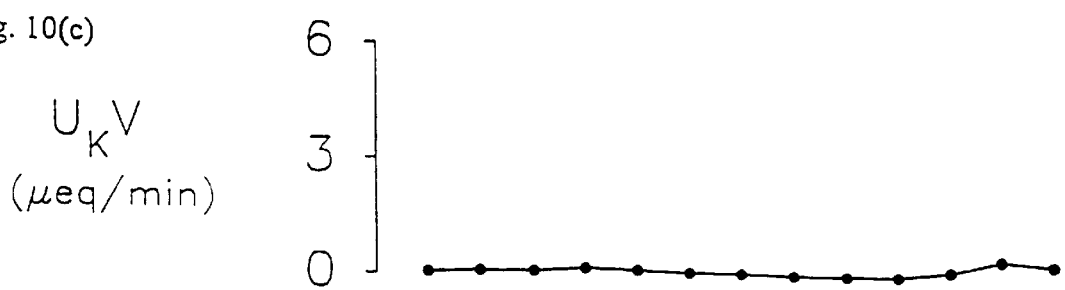
Figure 10D:
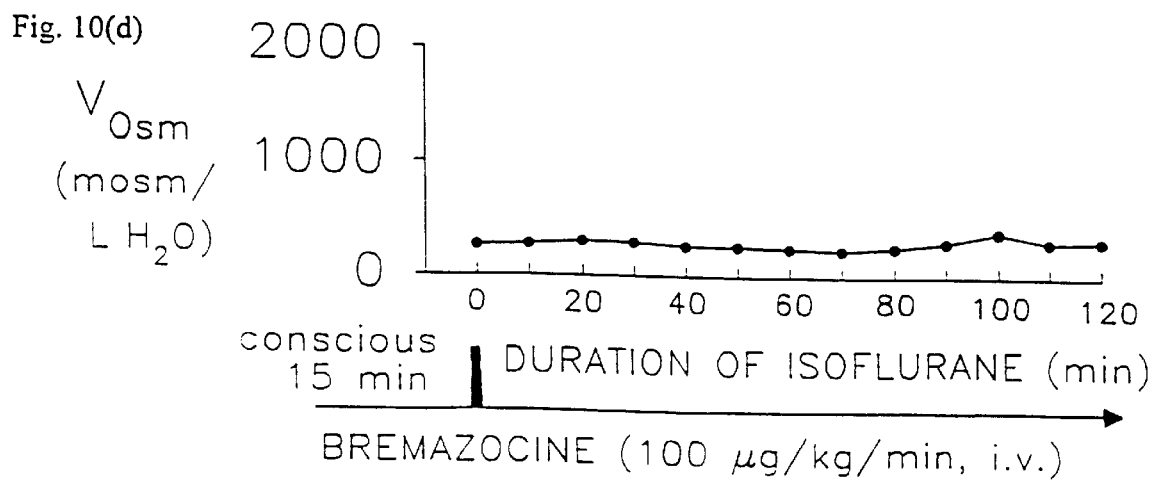

FIGS. 5(a)–(c) illustrate the effects of continuous intravenous infusion of U-50,488H on renal excretory function in a rat during surgery under isoflurane anesthesia.

FIGS. 6(a)–(d) depict the effects of pretreatment of a rat with the cis enantiomer of U-50,488H.

FIGS. 7(a)–(d) depict the effects of pretreatment with the kappa opioid agonist U-62,066E.

FIGS. 8(a)–(c) show the effects of a long-duration intravenous infusion of U-62,066E on renal function in a rat during surgery under isoflurane anesthesia.

FIGS. 9(a)–(d) depict the effects of pretreatment with the kappa opioid agonist U-69,593 on renal function in a rat.

FIGS. 10(a)–(d) depict the effects of pretreatment with the kappa opioid agonist bremazocine in a rat.

FIGS. 11(a)–(d) depict the effects of pretreatment with the kappa opioid agonist tifluadom in a rat.

Figure 12A:
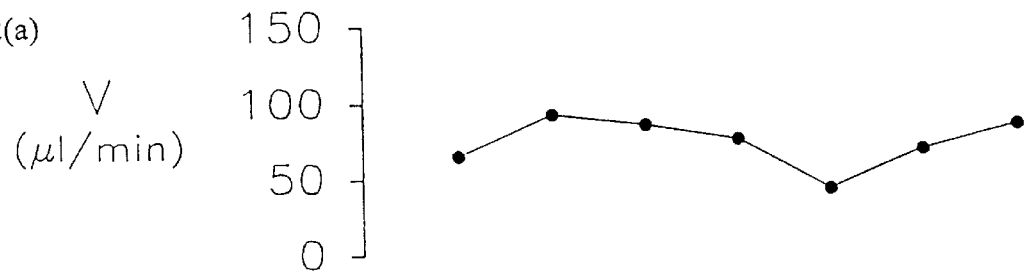
Figure 12B:
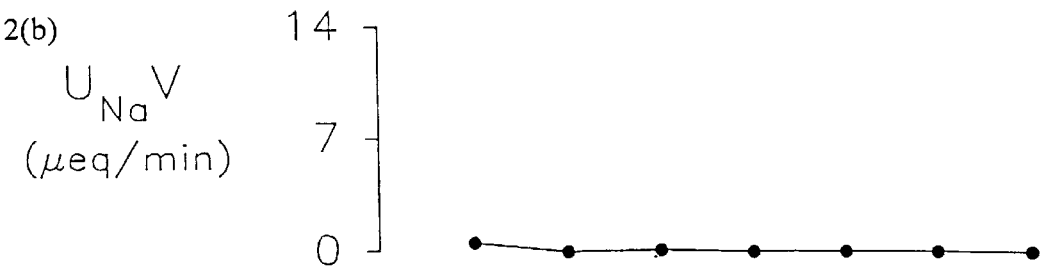
Figure 12C:
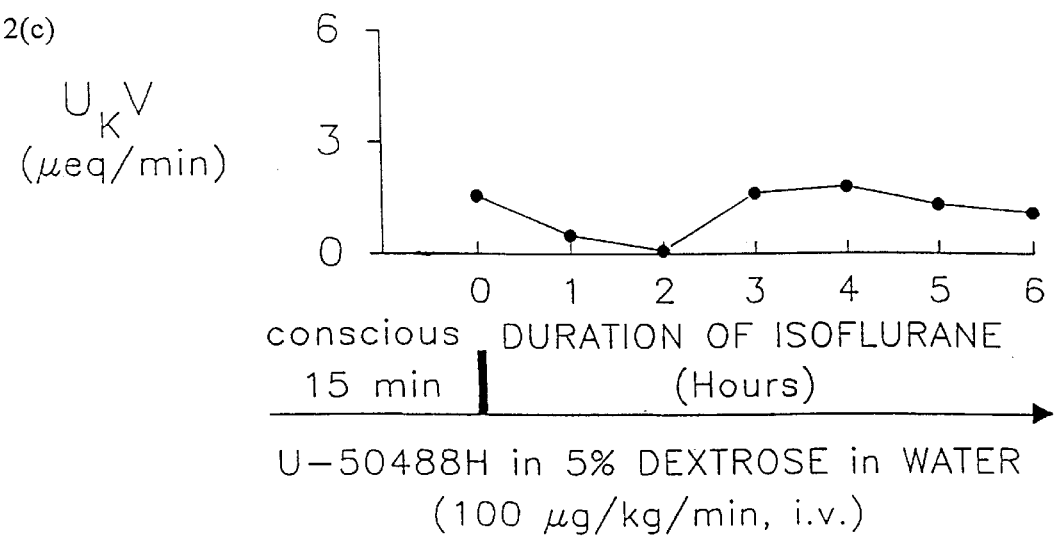

FIGS. 12(a)–(c) demonstrate the renal effects of an intravenous U-50,488H infusion in a rat during surgery and anesthesia, where the kappa agonist was dissolved in a solution of 5% dextrose in water instead of saline.

FIGS. 13(a)–(c) illustrate the renal responses produced by the high-ceiling loop diuretic furosemide in isoflurane-treated rats under surgery.

Figure 14A:
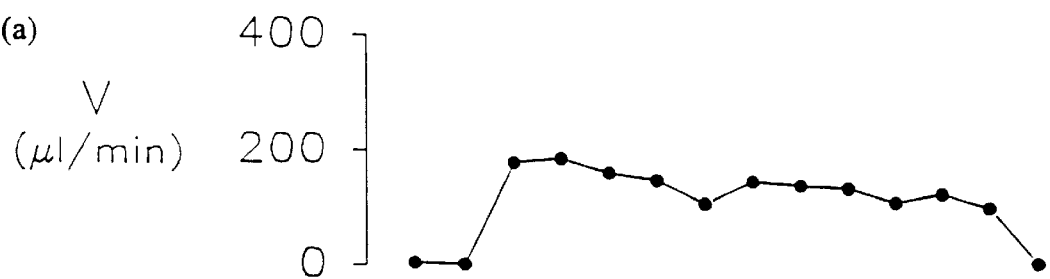
Figure 14B:
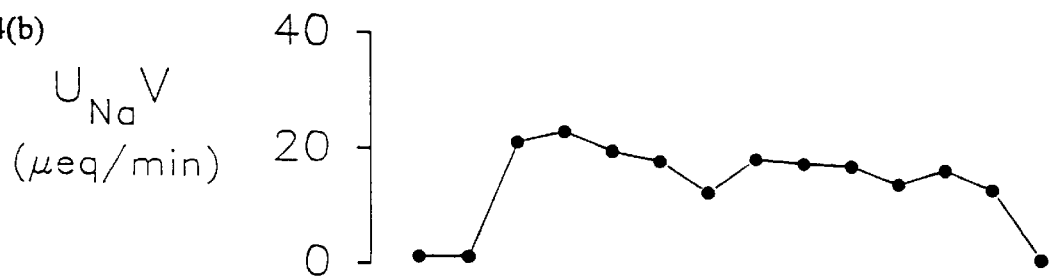
Figure 14C:
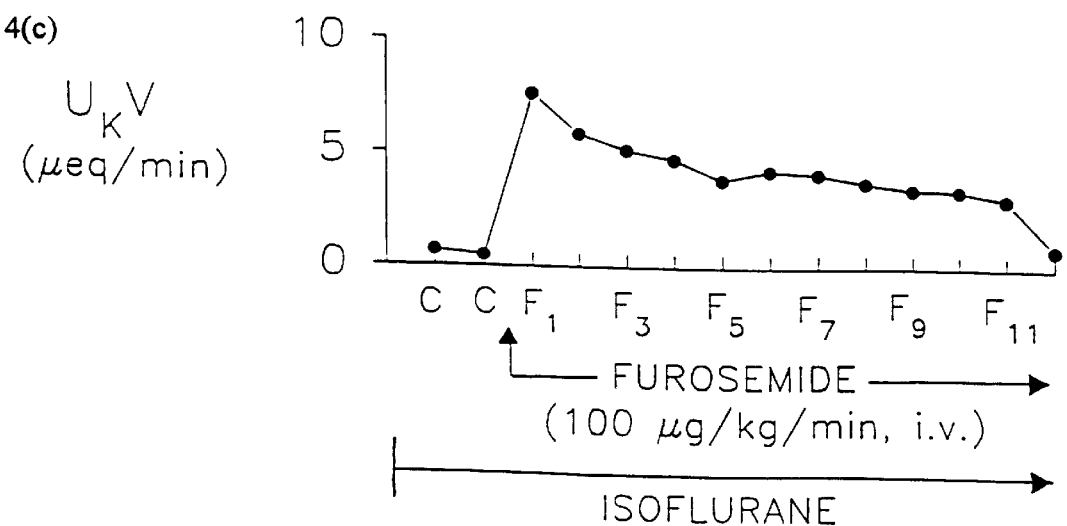

FIGS. 14(a)–(c) illustrate the effects of furosemide infusion on renal response during surgery and anesthesia.

Figure 15A:
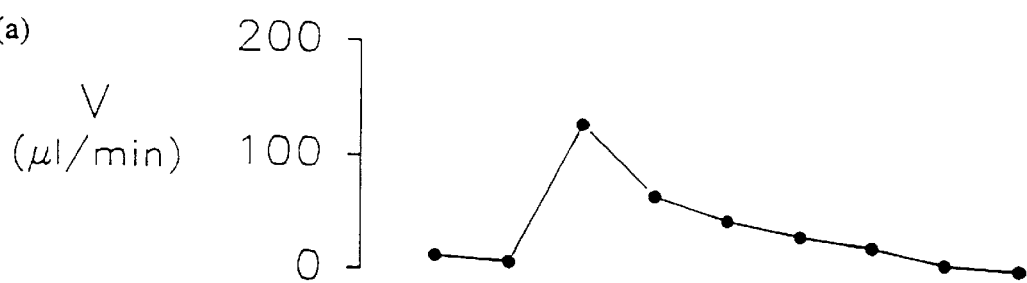
Figure 15B:
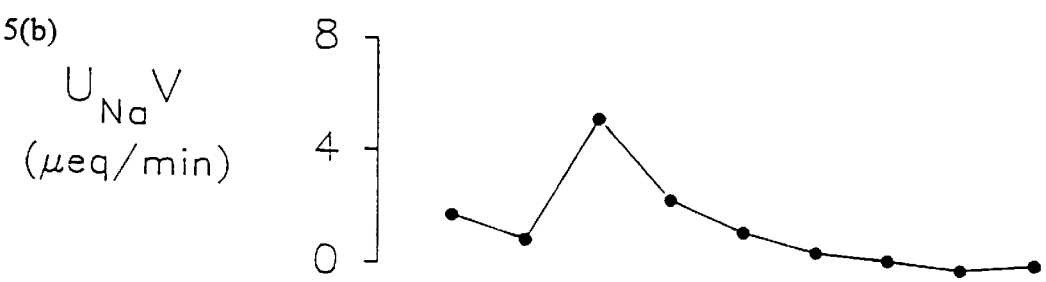
Figure 15C:
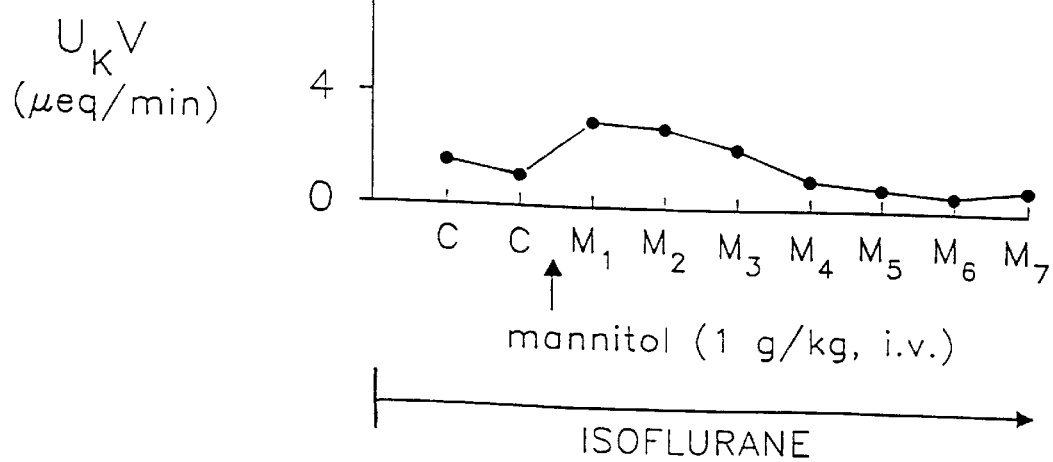

FIGS. 15(a)–(c) illustrate the effects of the osmotic diuretic mannitol on renal response during surgery and anesthesia.

FIGS. 1(a), 1(b), and 1(c) depict the levels of urine flow rate (V), urinary sodium excretion ($U_{Na}V$), and urinary potassium excretion ($U_KV$), respectively, that were observed in conscious Sprague-Dawley rats (n=5) under the following experimental conditions: cannula were implanted into the femoral artery and vein the day before surgery; a bladder catheter was implanted under methohexital (a short-acting barbiturate) anesthesia the day of the experiment, and rats were allowed to regain consciousness; all rats received an intravenous infusion of isotonic saline at a rate of 55 μl/minute during consecutive 10 minute urine collection periods, both during a control period (C) and for the duration of the study (periods S1–S6). During the control period (C), the levels of urine flow rate, urinary sodium excretion, and urinary potassium excretion were 42±7 $\mu$l/min, 7.6±0.5 $\mu$Eq/min, and 3.3±0.5 $\mu$Eq/min, respectively. As shown, urine flow rate, urinary sodium excretion, and urinary potassium excretion remained approximately steady in the conscious rats throughout the duration of study.

FIGS. 2(a)–(d) depict the renal responses of Sprague-Dawley rats (n=5) upon invasive surgery and isoflurane anesthesia, without any diuretic. As for the experiments depicted in FIG. 1, an intravenous infusion of isotonic saline at a rate of 55 $\mu$l/min was started in the conscious state, and was continued for the duration of the surgery and isoflurane anesthesia (200 minutes total). After 15 minutes of isotonic saline infusion while conscious, the rats were anesthetized by intravenous bolus administration of thiopental (25 mg/kg). Invasive surgery was then performed by implanting a urinary bladder catheter (PE-240) and performing a tracheotomy, the latter providing a convenient means for delivering gaseous anesthetic. Anesthesia was then maintained by administering isoflurane (1 MAC, minimum alveolar concentration as a percentage of total inspired gas) to the animals throughout the experimental protocol. Data are shown in FIGS. 2(a)–(d), respectively, for urine flow rate (V), urinary sodium excretion ($U_{Na}V$), urinary potassium excretion ($U_KV$), and urine osmolality ($V_{osm}$), during a thiopental control period (time 0), and at 10 minute intervals during isoflurane anesthesia. During surgery, urine flow rate and urinary sodium excretion were somewhat elevated during the thiopental control period (time 0). The start of isoflurane anesthesia, however, produced an immediate impairment of renal function. There was a substantial reduction in urine flow rate, dropping from 42 $\mu$l/min in the conscious rats (FIG. 1(a)) to less than 10 $\mu$l/min in the anesthetized animals (FIG. 2(a)). There was also a substantial reduction in urinary sodium excretion. The reduction in urine flow rate and in urinary sodium excretion were both sustained for the duration of the study. During the period of reduced urine output, there was a slight increase in urinary potassium excretion (FIG. 2(c)) (still below the control levels in FIG. 1(c)), as well as a slight increase in total urine osmolality over time (FIG. 2(d)).

FIGS. 3(a)–(d) illustrate the ability of the kappa opioid agonist U-50,488H (a benzeneacetamide derivative) to reverse the impairment of urine flow rate produced by the combination of surgery and isoflurane anesthesia. The U-50,488H was a gift from Upjohn Pharmaceuticals Kalamazoo, Mich.). As for the experiments depicted in FIG. 2, after surgery and the start of isoflurane anesthesia, consecutive 10-minute urine samples were collected during two isoflurane control periods during which isotonic saline was infused intravenously (55 $\mu$l/min). After these control urine collections, consecutive 10 minute experimental urine samples were taken during the intravenous infusion (55 $\mu$l/min) of isotonic saline containing U-50,488H (periods U1–U9). Abbreviations are the same as in FIG. 2. During control periods (C), surgery and isoflurane anesthesia impaired renal function and the urine flow rate (FIG. 3(a)). However, continuous intravenous infusion of U-50,488H (100 $\mu$g/kg/min) completely reversed the surgery and isoflurane-impaired urine flow. In fact, this kappa opioid agonist caused an "overshoot" in urine flow rate to about 120 $\mu$l/min, compared with the isotonic saline infusion rate of 55 $\mu$l/min. It is likely that the "overshoot" resulted from the large volume of fluid retained since the beginning of surgery and isoflurane administration. Despite the increase in urine flow rate, urinary sodium and potassium excretion remained at low levels throughout the duration of the study. These effects are novel; all current, clinically-used diuretics, whether used in surgical patients or conscious patients, cause increases not only in urine flow, but also in urinary sodium and potassium excretion rates.

FIGS. 4(a)–(d) demonstrate the effect of kappa agonist pretreatment on renal response during surgery and isoflurane anesthesia. Rats were infused intravenously for 15 minutes with the kappa opioid U-50,488H (100 $\mu$g/kg/min) (a benzeneacetamide derivative) while conscious. During continued U-50,488H infusion, anesthesia was induced by intravenous bolus administration of thiopental (25 mg/kg), and invasive surgery (tracheotomy and bladder catheter implantation) was performed. After surgery, urine (a 5 minute sample) was collected during a thiopental control period (time 0). Anesthesia was thereafter maintained by administering isoflurane to the animals through the tracheotomy tube. Consecutive 10-minute urine samples were collected during continued U-50,488H infusion (time 10–60). One hour after the start of isoflurane administration (time 60), the intravenous infusion of U-50,488H in isotonic saline was stopped. Rats were then infused intravenously with isotonic saline vehicle for the duration of the study (time 60–210). Abbreviations are the same as in FIG. 2. Pretreatment of rats with U-50,488H in the conscious state completely prevented the reduction in urine flow rate that is normally produced by surgery and isoflurane anesthesia (Compare FIG. 4(a) with FIG. 2(a)). Although urine output remained elevated during U-50,488H infusion (time 0–60 minutes), urinary sodium and potassium excretion remained low. In addition, intravenous infusion of U-50,488H reduced urinary calcium excretion in these animals (not illustrated). After the infusion of U-50,488H was stopped (time 60 minutes) and was replaced with isotonic saline alone, approximately 2½ hours passed before urine output was reduced. This period correlates well with the known 30-minute pharmacokinetic half-life of U-50,488H (2½ hours=30 minutes×5 half-lives). Urinary potassium excretion and urine osmolality tended to increase toward the end of the study (time 180–210).

FIGS. 5(a)–(c) illustrate the effects of continuous intravenous infusion of U-50,488H on renal excretory function in a single female Sprague-Dawley rat during surgery under isoflurane anesthesia. The experimental procedure was similar to that described for the experiments of FIG. 4, with the exception that U-50,488H was continuously infused intravenously for 10 hours after the start of isoflurane anesthesia. Abbreviations are as in FIG. 2. Pretreatment with U-50,488H prevented the initial anesthesia and surgery-induced shutdown of urine flow rate that normally results from these stressors at time 0–1 hours. In addition, intravenous infusion of U-50,488H continued to protect the kidneys from renal impairment over time. The urine flow rate remained elevated for the entire ten hour duration of U-50,488H infusion (time 1–10 hours), with some fluctuations. As previously observed in FIG. 4(c), urinary potassium excretion levels were low during the first hour of U-50,488H infusion. After the first hour, urinary potassium excretion rose slowly for a time (time 1–3 hours), and then more rapidly (time 4–10 hours). Urinary sodium excretion remained low for several hours (time 0–5 hours), but increased substantially after urinary potassium excretion had reached its peak (time 6–10 hours). It appeared that the changes in urinary sodium and potassium excretion were dissociated from one another, and that they occurred as different physiological mechanisms acted to override the action of U-50,488H on renal handling of sodium and potassium. Currently unknown mechanisms acted to prevent excessively high retention of these electrolytes in the body. Note that the levels of urinary potassium excretion toward the end of this study (time 8–10 hours), approached the levels observed in conscious rats during steady-state conditions (compare with FIG. 1(c)). The changes in urinary sodium excretion attained during continued U-50,488H infusion (time 7–10 hours) also reflect a similar mechanism, although it appeared that an 'overshoot' resulted due to a more avid initial retention of sodium than potassium. (Compare time 0–4 hours in FIGS. 5(b) and 5(c).) Kappa agonists are thus uniquely beneficial in that they can protect the kidneys from shutdown while maintaining constant urine output, without substantially inhibiting physiological compensatory mechanisms for the excretion of sodium and potassium when appropriate. Put differently, kappa opioid agonists do not substantially interfere with the regulatory mechanisms governing electrolyte homeostasis.

FIGS. 6(a)–(d) depict the effects of pretreatment of a single Sprague-Dawley rat with the cis enantiomer of U-50, 488H. In contrast to the active kappa opioid agonist, trans-(+/−)-U-50,488H, the cis-U-50,488H enantiomer has previously been shown to be devoid of activity at kappa opioid receptors. The same experimental protocol was used as described above for the experiments of FIG. 4, except that the study was terminated after 60 minutes of intravenous infusion (55 $\mu$l/min) of the inactive cis-U-50,488H enantiomer. Abbreviations are as for FIG. 2. After the rat was pretreated in the conscious state with cis-U-50,488H, the urine flow rate was 22 $\mu$l/min during thiopental anesthesia and surgery (time 0). After the start of isoflurane anesthesia (time 10–60 min), urine flow rate decreased to 7 $\mu$l/min (time 20 min), and remained at this low level for the duration of the study. During continuous infusion of cis-U-50,488H, urinary sodium excretion decreased substantially reduced during isoflurane anesthesia (FIG. 6(b)). These results demonstrated that the cis-enantiomer of U-50,488H failed to protect kidneys from the shutdown evoked by anesthesia and surgery. These data also support the conclusion that the renal protective action of kappa opioid agonists involves stimulation of kappa opioid receptors.

FIGS. 7(a)–(d) depict the effects of pretreatment with a different kappa opioid agonist, U-62,066E (spiradoline, a benzeneacetamide derivative). U-62,066E was purchased from Research Biochemicals International (Natick, Mass.). Rats (two male and two female) underwent the same experimental protocol as described for the experiments of FIG. 4, except that the kappa agonist U-62,066E was infused intravenously (55 $\mu$l/min) instead of U-50,488H. Since U-62,066E evoked similar responses in male and female rats in these studies, data for both sexes were pooled together in FIGS. 6(a)–(d). Abbreviations are as for FIG. 2. After the rats were pretreated in the conscious state with U-62,066E, urine flow rate was 87±12 $\mu$l/min during thiopental anesthesia (time 0). After the start of isoflurane anesthesia, urine flow rate decreased and reached a plateau at a mean level of approximately 45 $\mu$l/min (time 30–60). After stopping the U-62,066E infusion (time 60), urine flow rate remained approximately constant at this level for an additional 120 minutes (time 60–180). Throughout the duration of the study, urinary sodium excretion remained low. In contrast, urinary potassium excretion showed a gradual increase over the duration of the study. The effects of U-62,066E were generally similar to those shown in FIG. 4 for rats treated with U-50,488H.

FIGS. 8(a)–(c) show the effects of a long-duration intravenous infusion of U-62,066E on renal excretory function in a single male Sprague-Dawley rat during surgery under isoflurane anesthesia. The experimental procedure was similar to that described for the experiment of FIG. 6, except that the kappa agonist infusion was continued for 6 hours after the start of isoflurane anesthesia. Abbreviations are as in FIG. 2. Pretreatment with U-62,066E prevented impairment of urine flow rate during surgery and anesthesia. During continued infusion of U-62,066E, urine flow rate remained elevated throughout the 6 hours of the study. Although urinary sodium excretion remained low throughout the duration of the experiment (time 0–6 hours), urinary potassium excretion showed a significant and steady increase toward a new plateau level. These patterns of change were similar to those produced by long duration administration of the kappa opioid U-50,488H (see FIG. 5).

FIGS. 9(a)–(d) depict the effects of pretreatment with a different kappa opioid agonist, U-69,593 (a benzeneacetamide derivative) in a single rat. U-69,593 was purchased from Research Biochemicals International, Natick, Mass. For this study the same experimental protocol was used as described above for the experiments of FIG. 4, except that the kappa agonist U-69,593 was infused intravenously (55 $\mu$l/min) instead of U-50,488H, for a total of 120 minutes. After the 120 minute experimental urine collection, the experiment was terminated. Abbreviations are as for FIG. 2. After the rat was pretreated in the conscious state with U-69,593 (100 $\mu$g/kg/min), urine flow rate was 39 $\mu$l/min during thiopental anesthesia and surgery (time 0). After the start of isoflurane anesthesia, urine flow rate showed an initial increase to 54 $\mu$l/min (time 10), after which it decreased to 13 $\mu$l/min (time 20). Despite this reduction, urine flow rate thereafter increased steadily over the duration of the study (time 30–120). Throughout the study, urinary sodium and potassium excretion and urine osmolality remained low. The effects of U-69,593 were generally similar to those shown in FIG. 4 and FIG. 7 for rats treated with U-50,488H and U-62,066E, respectively. The observation that U-69,593 did not completely prevent a decrease in urine output to isoflurane (time 20 min) suggests that a higher infusion dose of this kappa agonist may be required for complete renal protection.

FIGS. 10(a)–(d) depict the effects of pretreatment with a different kappa opioid agonist, bremazocine (a benzomorphan derivative) in a single rat. Bremazocine was a gift from the research technology branch of the National Institute for Drug Abuse (NIDA). The same experimental protocol was used as described above for the experiment of FIG. 9, except that the kappa agonist bremazocine was infused intravenously (55 $\mu$l/min) instead of U-69,593 for a total of 120 minutes. Abbreviations are as for FIG. 2. After the rat was pretreated in the conscious state with bremazocine (100 $\mu$g/kg/min), urine flow rate was 37 $\mu$l/min during thiopental anesthesia and surgery (time 0). After the start of isoflurane anesthesia, urine flow rate remained constant at this level with only minor fluctuations for the two hour duration (time 10–120). Urinary sodium and potassium excretion and urine osmolality remained low throughout the study. The effects of bremazocine were similar to those shown in FIG. 4, FIG. 7, and FIG. 9 for rats treated with U-50,488H, U-62,066E, and U-69,593, respectively. These results demonstrated that in addition to the benzeneacetamides (e.g. U-50,488H, U-62,066E, U-69,593, etc.), benzomorphan derivative kappa agonists also provide renal protection during surgery under general anesthesia.

FIGS. 11(a)–(d) depict the effects of pretreatment with a different kappa opioid agonist, tifluadom (a benzodiazepine derivative) in a single rat. Tifluadom was a gift from Dr.

Joseph M. Moerschbaecher, Department of Pharmacology, Louisiana State University Medical Center (New Orleans, La.). For this study the same experimental protocol was used as described above for the experiment of FIG. 9, except that the kappa agonist tifluadom was infused intravenously (55 µl/min) instead of U-69,593 for a total of 120 minutes. Abbreviations are as for FIG. 2. After the rat was pretreated in the conscious state with tifluadom (50 µg/kg/min), urine flow rate was 20 µl/min during thiopental anesthesia and surgery (time 0). After the start of isoflurane anesthesia, urine output remained steady (time 10) and consistently increased over time (time 20–90) until a plateau was reached (time 100–120). Urinary sodium and potassium excretion and urine osmolality remained low throughout the study. The effects of tifluadom were similar to those shown in FIG. 4, FIG. 7, FIG. 9 and FIG. 10 for rats treated with U-50, 488H, U-62,066E, U-69,593, and bremazocine, respectively. These results demonstrated that in addition kappa agonists of the benzeneacetamide (e.g. U-50,488H, U-62, 066E, U-69,593, etc.), and benzomorphan (e.g. bremazocine) classification, the benzodiazepine derivative kappa opioid agonists also provide renal protection during surgery under general anesthesia.

The experiments described thus far examined the renal responses to intravenous infusions of kappa agonists dissolved in isotonic saline. FIGS. 12(a)–(c) demonstrate the renal effects of an intravenous U-50,488H infusion in a single rat during surgery and anesthesia, where the kappa agonist was instead dissolved in a solution of 5% dextrose in water ($D_5W$, osmolarity=252 mosm/L). The experimental methods were otherwise the same as those described for FIG. 8. Abbreviations are as in FIG. 2. Pretreatment and continued infusion of the rat with U-50,488H in $D_5W$ maintained urine output during surgery and anesthesia for the duration of the study (time 0–6 hours). Urinary potassium excretion showed an initial decrease (time 1–2 hours), but returned to a steady level, where it remained through the end of the study (time 3–6 hours). Urinary sodium excretion remained low at all times (time 0–6 hours).

For comparison, FIGS. 13(a)–(c) illustrate the renal responses produced by the high-ceiling loop diuretic furosemide in isoflurane-treated rats under surgery. As in the other studies, rats were infused intravenously with isotonic saline at a rate of 55 µl/min for the duration of the study. Thirty minutes after the start of isoflurane anesthesia, consecutive 10-minute urine samples were collected during two isotonic saline control periods (C), and after an intravenous bolus injection of furosemide (F1–F6). Abbreviations are the same as for FIG. 2. During the control periods (C) urine flow rate was significantly reduced by isoflurane anesthesia. As shown in FIG. 13(a), following bolus administration of furosemide, the urine flow rate initially increased to extremely high levels (about 300 µl/min), and then declined rapidly. As shown in FIGS. 13(b) and (c), furosemide caused a large urinary loss of sodium and potassium. Although furosemide can induce a diuretic response during surgery and anesthesia, it also causes large changes in body fluid compartments. In addition, unlike the kappa opioids, furosemide causes a substantial loss of sodium and potassium. Such large shifts in body water and electrolyte composition are undesirable during surgery. FIGS. 14(a)–(c) illustrate the effects of furosemide infusion on renal response during surgery and anesthesia. The protocol described in connection with FIG. 5 was repeated, except that furosemide (instead of a kappa agonist) was infused intravenously over the duration of the study. Intravenous infusion of furosemide caused large increases in urine flow rate (up to about 200 µl/min), in urinary sodium excretion, and in urinary potassium excretion. These renal responses were immediate in onset. In contrast to the bolus administration, furosemide infusion caused the urine flow rate, urinary sodium excretion, and urinary potassium excretion to remain at high levels for about 110 minutes (periods F1–F11). Finally, after 120 minutes of continued furosemide infusion (F12), the excretion rates of water, sodium, and potassium returned to the impaired pre-drug levels.

For comparison, FIGS. 15(a)–(c) illustrate the effects of i.v. bolus administration of the osmotic diuretic mannitol on renal response during surgery and anesthesia. The protocol described above for FIG. 13 was repeated in isoflurane-anesthetized rats under surgery, except that mannitol (instead of a kappa agonist or a loop diuretic) was injected intravenously. Bolus injection of mannitol caused a large increase in urine flow rate (up to 135 µl/min) that was immediate in onset. Mannitol also caused an increase in urinary sodium and potassium excretion, but the magnitude of these changes was considerably less than that produced by furosemide (see FIGS. 13 and 14). Despite the profound diuretic response initially produced by mannitol, the increase in urine flow rate was not maintained and declined to the impaired levels observed before drug administration.

Kappa opioid agonists may be administered to humans or other mammals in pharmaceutical compositions or formulations in combination with one or more pharmaceutically acceptable carriers known in the art. Suitable pharmaceutical adjuvants for injecting solutions include stabilizing agents, solubilizing agents, buffers, and viscosity regulators. Examples of these adjuvants include but are not limited to ethanol, ethylenediamine tetraacetic acid, tartrate buffers, citrate buffers, and high molecular weight polyethylene oxide viscosity regulators. These pharmaceutical formulations may be injected intramuscularly, intraperitoneally, or intravenously, although intravenous injection/infusion is preferred. The preferred doses of kappa agonist pretreatments will depend on the particular compound used, and are typically about 2–10 times, preferably about 4–5 times the dose required to produce a substantial diuretic response in a conscious individual.

Any pharmacologically acceptable kappa opioid agonist will function the present invention, as the underlying mechanism appears to depend upon binding to and stimulating kappa opioid receptors. There are at least five major categories of kappa opioid agonists: (1) the dynorphins, which are endogenous peptides and their derivatives; (2) the benzodiazepine derivatives, such as tifluadom; (3) the benzomorphan derivatives, such as ethylketocyclazocine, ketocyclazocine, and bremazocine; (4) the benzeneacetamide derivatives, such as U-50,488H, U-62,066E, U-69,593, CI-977, and PD 117302; and (5) the aminomethylpyridines, such as BRL 52537, BRL 52656, BRL 53114, GR89696, GR86014, and GR91272.

Illustrative examples of kappa opioid agonists are listed below. In many cases the listings include references to a commercial source, a citation for the synthesis of a compound, or both.

1. L Kappa Opioid Agonists available through SmithKline Beecham Pharmaceuticals, Department of Renal Pharmacology, King of Prussia, Pa.; or Department of Biology, SmithKline Beecham Farmaceutici, Baranzate, Milan, Italy:

BRL 52537 (2S)-1-[3,4-dichlorophenylacetyl]-2-[(1-pyrrolidinylmethyl]-piperidine BRL 52656 (2S)-1-[[4-trifluoromethyl-phenyl]acetyl]-2-[(1-pyrrolidinyl)methyl]piperidine V. Vecchietti et al., *J. Med. Chem.*, vol. 34, pp. 397–403 (1991).

BRL 53114 (–)-1-(4-trifluoromethylphenyl)-acetyl-2-(1-pyrrolidinylmethyl)-3,3-dimethyl-piperidine hydrochloride BRL 52974 4-(1-pyrrolidinylmethyl)-5-(3,4-dichlorophenyl)acetyl-4,5,6,7-tetrahydroimidazo-[4,5-c]-pyridine BRL 53117 1-[(3,4-dichlorophenyl)acetyl]-2-[(3-hydroxy-1-pyrrolidinyl)-methyl]-4,4-dimethylpiperidine BRL 52974 5-[(3,4-dichlorophenyl)acetyl]-4-(1-pyrrolidinylmethyl)-4,5,6,7-tetrahydro-1H-imidazo[4,5-c] pyridine BRL 53001 (2S)-2-(dimethylaminomethyl)-1-[(5,6,7,8-tetrahydro-5-oxo-2-naphthyl)acetyl]piperidine 2-(aminomethyl)piperidine derivatives, with incorporation of the 1-tetralon-6-yl-acetyl residue:

G. Giardina et al., *J. Med. Chem.*, vol. 37, pp. 3482–3491 (1994)

Compound (34) (2S)-2-[(dimethylamino)-methyl]-1-[(5,6,7,8-tetrahydro-5-oxo-2-naphthyl)-acetyl]-piperidine II. Kappa Opioid Agonists available through The Upjohn Company, Kalamazoo, Mich.:

U-50,488H trans-(+/–)-3,4-dichloro-N-methyl-N-[2-(1-pyrrolidinyl)cyclohexyl]-benzeneacetamide methanesulphonate hydrate J. Szmuszkovicz et al., *J. Med. Chem.*, vol. 25, pp. 1125–1126 (1982); U.S. Pat. No. 4,098,904; U.S. Pat. No. 4,145,435; European Pat. No. 0 129 991 (1985); Chem. Abstr. vol. 91, no. 39003g (1979).

U-62,066E (spiradoline) 3,4-dichloro-N-methyl-N-(3-methylene-2-oxo-8-(1-pyrrolidinyl)-1-oxaspiro(4,5)dec-7-yl)-benzeneacetamide J. Szmuszkovicz et al., *J. Med. Chem.*, vol. 25, pp. 1125–1126 (1982); U.S. Pat. No. 4,438,130; *Chem Abstr.* vol. 101, no. 54912w; German Pat. No. 3241933 (1985); *Chem. Abstr.* vol. 103, no. 184969b (1985).

U-69,593 (5-α,7-α,8-β)-(–)-N-methyl-N-[7-(1-pyrrolidinyl)-1-oxaspiro(4,5)-dec-8-yl]benzeneacetamide R. A. Lahti et al., *Eur. J. Pharmacol.*, vol. 109, pp. 281–284 (1985).

III. Kappa Opioid Agonists available through Parke-Davis Research Unit, Addenbrooke's Hospital Site, Hills Road, Cambridge, England, or Parke-Davis Research Division, Warner-Lambert Company, Ann Arbor, Mich.

CI-977 (enadoline=PD 129290) (5R)-(5-α, 7-α, 8-β)-N-methyl-N-[7-(1-pyrrolidinyl)-1-oxaspiro[4,5]dec-8-yl]-4-benzo-furanacetamide monohydrochloride P. R. Halfpenny et al., *J. Med. Chem.*, vol. 33, pp. 286–291 (1990); P. R. Halfpenny et al., *J. Med. Chem.*, vol. 34, pp. 190–194 (1991).

PD 117302 (+/–)-trans-N-methyl-N-[2-(1-pyrrolidinyl)-cyclohexyl]-benzo[b]-thiophene-4-acetamide monohydrochloride C. R. Clark et al., *J. Med. Chem.*, vol. 31, pp. 831–836 (1988).

Derivatives of PD 117302:

A. Compound (9) (+)-N-methyl-N-[7-(1-pyrrolidinyl)-1-oxaspiro[4.5]dec-8-yl]acenaphthene-carboxamide monohydrochloride P. R. Halfpenny et al., *J. Med. Chem.*, vol. 34, pp. 190–194 (1989).

B. Compound (17) (–)-4,5-dihydro-N-methyl-N-[7-(1-pyrrolidinyl)-1-oxaspiro[4.5]dec-8-yl]-3H-naphtho-[1,8-b,c]-thiophene-5-carboxamide-p-toluene sulfonate P. R. Halfpenny et al., *J. Med. Chem.*, vol. 34, pp. 190–194 (1989).

C. Compound (32) trans-(+/–)-N-methyl-N-[4,5-dimethoxy-2-(1-pyrrolidinyl)-cyclohexyl]-benzo[b]-thiophene-4-acetamide P. R. Halfpenny et al., *J. Med. Chem.*, vol. 32, pp. 1620–1626 (1989).

D. Compound (21) (–)-(5-β, 7-β, 8-α)-N-methyl-N-[7-(1-pyrrolidinyl)-1-oxaspiro[4.5]-dec-8-yl]-benzo[b]furan-4-acetamide monohydrochloride P. R. Halfpenny et al., *J. Med. Chem.*, vol. 33, pp. 286–291 (1990).

IV. Kappa Opioid Agonists available through Zambeletti Research Laboratories, Baranzate, Milan, Italy (2S)-1-(arylacetyl)-2-(aminomethyl)piperidine derivatives:

V. Vecchietti et al., *J. Med. Chem., vol.* 34, pp. 397–403 (1991); V. Vecchietti et al., *J. Med. Chem.*, vol. 34, pp. 2624–2633 (1991).

A. Compound (14) (=BRL 52537A) (2S)-1-[3,4-dichlorophenyl-acetyl]-2-(pyrrolidin-1-yl-methyl) piperidine hydrochloride B. Compound (21) (=BRL 52656A) (2S)-1-[[4-(trifluoromethyl)phenyl]acetyl]-2-(pyrrolidin-1-yl-methyl) piperidine hydrochloride (1S)-1-(aminomethyl)-2-(arylacetyl)-1,2,3,4-tetrahydroisoquinoline and heterocycle-condensed tetrahydropyridine derivatives:

V. Vecchietti et al., *J. Med. Chem.*, vol. 34, pp. 2624–2633 (1991).

A. Compound (28)
B. Compound (30)
C. Compound (48)

V. Kappa Opioid Agonists available through The Du Pont Merck Pharmaceutical Co., Wilmington, Del.

DuP747 3,4-dichloro-N-methyl-N-(2-(pyrrolidin-1-yl)-1,2, 3,4-tetrahydro-5-hydroxynaphthalen-1-yl)-benzeneacetamide M. A. Hussain et al., *Pharm. Res.*, vol. 9, pp. 750–752 (1992).

DuP E3800 (+/–)-trans-3,4-dichloro-N-methyl-[2-(pyrrolidine-1-yl)-6-hydroxy- 1,2,3,4tetrahydronaphth-1-yl]-benzeneacetamide phosphate V. Kappa Opioid Agonists available through Preclinical Pharmaceutical Research, and Department of Medicinal Chemistry, E. Merck, Darmstadt, Germany; or Merck-Clevenot S. A., Nogent-sur-Marne, France EMD 60400 N-methyl-N-[(1S)-1-phenyl-2-((3S)-3-hydroxypyrrolidine-1-yl)-ethyl]-2-aminophenylacetamide 2HCl A. Barber et al., *Br. J. Pharmacol.*, vol. 111, pp. 843–851 (1994).

EMD 61753 R. Gottschlich et al., *Chirality*, vol. 6, pp. 685–689 (1994); A. Barber et al., *Br. J. Pharmacol.*, vol. 113, pp. 1317–27 (1994).

VI. Kappa Opioid Agonists available through Glaxo Group Research Ltd., Dept. of Medicinal Chemistry and Neuropharmacology, Ware, Herefordshire, England:

1-[(3,4-dichlorophenyl)acetyl]-2-[(alkylamino)methyl] piperidine derivatives:

D. Scopes et al., *J. Med. Chem., vol.* 35, pp. 490–501 (1992); A. Hayes et al., *Br. J. Pharmacol.*, vol. 101, pp. 944–948 (1990); H. Rogers et al., *Br. J. Pharmacol.,* vol. 106, pp. 783–789 (1992).

A. Compound (10) 1-[3,4-dichlorophenyl-acetyl]-2-[1-(3-oxopyrrolidinyl)]methyl]piperidine B. Compound (39) (=GR 45809) 8-[3,4-dichlorophenyl-acetyl]-7-(1-pyrrolidinylmethyl)-1,4-dioxa-8-azaspiro[4,5] decane C. GR89696 methyl-4-[3,4-dichlorophenyl-acetyl]-3-(1-pyrrolidinylmethyl)-1-piperazinecarboxylate fumarate D. GR86014 2-[(3,4-dichlorophenyl)acetyl]-1,2,3,4-tetrahydro-1-(1-pyrrolidinyl-methyl)-5isoquinolinol maleate E. GR91272 5-[(3,4-dichlorophenyl)-acetyl]-4,5,6,7-tetrahydro-4-[(3-hydroxy-1-pyrrolidinyl)-methyl]furo[3,2-c]pyridine hydrochloride F. GR44821 1-[(3,4-dichlorophenyl)acetyl]-2-[(3-oxo-1-pyrrolidinyl)methyl]piperidine maleate G. GR103545 (R)-methyl-4-[(3,4-dichlorphenyl)acetyl]-3-(1-pyrrolidinyl-methyl)-1-piperazinecarboxylate fumarate

H. GR94839

I. GR85571

5-(arylacetyl)-4-[(alkylamino)methyl]furo[3,2-c]pyridines:

A. Naylor et al., J. Med. Chem., vol. 37, pp. 2138–44 (1994).
A. Compounds (16–23)
B. Compound (26) (=GR107537)
C. Compound (27)

Substituted trans-3-(decahydro- and octahydro-4a-isoquinolinyl) phenols:

D. Judd et al., J. Med. Chem., vol. 35, pp. 48–56 (1992).
A. Compound (10)
B. Compounds (11 a–d)
C. Compound (20)

VII. Kappa Opioid Agonists available through ICI Pharmaceutical, Research Department, Alderley Park, Macclesfield, Cheshire, England G. Costello et al., Eur. J. Pharmacol, vol. 151, pp. 475–478 (1988).

ICI 204879 (R,S)-N-[2-(N-methyl-3,4-dichlorophenylacetamido)-2-(3,4-dimethyloxyphenyl)-ethyl]pyrrolidine hydrochloride ICI 199441 (2S)-N-[2-(N-methyl-3,4-dichlorophenylacetamido)-2-phenylethyl]pyrrolidine hydrochloride ICI 197067 (2S)-N-[2-(N-methyl-3,4-dichlorophenylacetamido)-3-methylbutyl]pyrrolidine hydrochloride 2-(3,4-dichlorophenyl)-N-[2-(1-pyrrolidinyl)ethyl] acetamide derivatives (U-50,488 derivatives):

G. Costello et al., J. Med. Chem., vol. 34, pp. 181–189 (1991).
A. Compound (8) 2-(3,4-dichlorophenyl)-N-methyl-N-[(1S)-1-phenyl-2-(1-pyrrolidinyl)ethyl]acetamide 2-(3,4dichlorophenyl)-N-methyl-N-[2-(1-pyrrolidinyl)-1-substituted-ethyl]acetamides:

J. Barlow et al., J. Med. Chem., vol. 34, pp. 3149–3158 (1991).
A. Compound (13) 2-(3,4-dichlorophenyl)-N-methyl-N-[(1S)-1-(1-methylethyl)-2-(1-pyrrolidinyl)-ethyl]acetamide
B. Compound (48) 2-(3,4-dichlorophenyl)-N-methyl-N-[(1R,S)-1-(3-aminophenyl)-2-(1-pyrrolidinyl)-ethyl]acetamide VII. Kappa Opioid Agonists available through Medizinische Klinik II and Institut fur Klinische Chemie, Klinikum Grosshadern, München, Germany; or Humanpharmakologisches Zentrum, Boehringer Ingelheim KG, Ingelheim am Rhein, Germany MR 2033 (+)-α-(1R,5R,9R)-5,9-dimethyl-2-(L-tetrahydrofurfuryl)-2'-hydroxy-6,7-benzomorphan MR 2034 (−)-α-(1R, 5R,9R)-5,9-dimethyl-2-(L-tetrahydrofurfuryl)-2'-hydroxy-6,7-benzomorphan H. Merz et al., J. Med. Chem., vol. 22, pp. 1475–1479 (1979).

IX. Kappa Opioid Agonist available through Preclinical Research, Pharmaceutical Division, Sandoz Ltd., Basel, Switzerland; or Kali-Chemie Pharma Ltd., Hannover, Germany tifluadom (+)-(1-methyl-2,3-thienyl-carboxyl)-aminomethyl-5-(2-fluorophenyl)-H-2,3-dihydro-1,4-benzodiazepine D. Römer et al., Life Sciences, vol. 31, pp. 1217–1220 (1982).

X. Kappa Opioid Agonist available through Centre de Recherches Roussel Uclaf, Romainville, France; or Hôp. Sacré-Coeur, Université de Montréal, Canada RU 51599 (Niravoline)

G. Hamon et al., J. Am. Soc. Nephrol, vol. 5, p. 272A (1994).

XI. Dynorphin, Dynorphin Derivatives, and Analogs available through Sigma, RBI, ICN, and other pharmaceutical and biochemical distributors:

G. Martinka et al., Eur. J. Pharmacol., vol. 196, pp. 161–167 (1991).
A. Dynorphin A-(1–11)-$NH_2$
B. [D-Ala$^3$]Dyn A(1–11)-$NH_2$
C. [Ala$^3$]Dyn A(1–11)-$NH_2$ F. Lung et al.,J. Med. Chem., vol. 38, pp. 585–586 (1995).

XII. Kappa Opioid Agonist available through EISAI Chemical Co., Tsukuba Research Laboratories, Ibaraki, Japan:

Benzomorphans ketocyclazocine (+)-3-(cyclopropylmethyl)-8-keto-5-(eq)-9(ax)-dimethyl-6,7-benzomorphan bremazocine [5R-(5,7,8-β)]-N-methyl-N-[7-(1-pyrrolidinyl)-1-oxaspiro]-4,5-[dec-8-yl]-4-benzofuranacetamide XIII. Other Kappa Opioid Agonists
ethylketocyclazocine (Sterling Winthrop)
HN-11608 (Harslund Nycomed)
RP-60180 (Rorer)
TRK-820 (Toray)
R-84760

The entire disclosures of all references cited in the specification are hereby incorporated by reference in their entirety. In the event of an otherwise irresolvable conflict, however, the present specification shall control.

I claim:

1. A method for inducing urine flow in a human; wherein the human is undergoing surgery or is experiencing severe trauma; said method comprising placing the human under general anesthesia with a gaseous, inhaled anesthetic agent; and administering to the human U-62,066E (3,4-dichloro-N-methyl-N-(3-methylene-2-oxo-8-(1-pyrrolidinyl)-1-oxaspiro(4,5)dec-7-yl)benzeneacetamide), in an amount effective to increase urine flow.

2. A method as recited in claim 1, wherein the U-62,066E is administered in an amount effective to prevent the renal loss of sodium, potassium, or plasma osmolality.

3. A method as recited in claim 2, wherein the U-62,066E is continuously administered intravenously during a period beginning prior to the general anesthesia, and continuing during the general anesthesia, wherein the period of administration of the U-62,066E begins sufficiently before the general anesthesia that no substantial decrease in urine flow occurs upon the onset of the general anesthesia.

4. A method as recited in claim 3, wherein the U-62,066E is continuously administered intravenously during a period beginning prior to the general anesthesia, and continuing during the general anesthesia, wherein the period of administration of the U-62,066E begins sufficiently before the general anesthesia that no substantial renal loss of sodium, potassium, or osmolality occurs upon the onset of the general anesthesia.

5. A method as recited in claim 1, wherein the U-62,066E is continuously administered intravenously during a period beginning prior to general anesthesia, and continuing during general anesthesia, wherein the period of administration of the U-62,066E begins sufficiently before the general anesthesia that plasma sodium, plasma potassium, or plasma osmolality are maintained at physiologically acceptable levels upon the onset of general anesthesia.

6. A method as recited in claim 5, wherein the period of administration of the U-62,066E begins at least fifteen minutes before the general anesthesia.

7. A method as recited in claim 5, wherein the period of administration of the U-62,066E begins at least thirty minutes before the general anesthesia.

8. A method as recited in claim 1, wherein the U-62,066E is administered intramuscularly or subcutaneously prior to the general anesthesia.

9. A method for inducing urine flow in a human; wherein the human is undergoing surgery or is experiencing severe trauma; said method comprising placing the human under general anesthesia with a gaseous, inhaled anesthetic agent; and administering to the human CI-977 ((5R)-(5-α,7-α,8-β)-N-methyl-N-[7-(1-pyrrolidinyl)-1-oxaspiro[4,5]dec-8-yl]-4-benzo-furanacetamide monohydrochloride) in an amount effective to increase urine flow.

10. A method as recited in claim 9, wherein the CI-977 is administered in an amount effective to prevent the renal loss of sodium, potassium, or plasma osmolality.

11. A method as recited in claim 10, wherein the CI-977 is continuously administered intravenously during a period beginning prior to the general anesthesia, and continuing during the general anesthesia, wherein the period of administration of the CI-977 begins sufficiently before the general anesthesia that no substantial decrease in urine flow occurs upon the onset of the general anesthesia.

12. A method as recited in claim 11, wherein the CI-977 is continuously administered intravenously during a period beginning prior to the general anesthesia, and continuing during the general anesthesia, wherein the period of administration of the CI-977 begins sufficiently before the general anesthesia that no substantial renal loss of sodium, potassium, or osmolality occurs upon the onset of the general anesthesia.

13. A method as recited in claim 9, wherein the CI-977 is continuously administered intravenously during a period beginning prior to general anesthesia, and continuing during general anesthesia, wherein the period of administration of the CI-977 begins sufficiently before the general anesthesia that plasma sodium, plasma potassium, or plasma osmolality are maintained at physiologically acceptable levels upon the onset of general anesthesia.

14. A method as recited in claim 13, wherein the period of administration of the CI-977 begins at least fifteen minutes before the general anesthesia.

15. A method as recited in claim 13, wherein the period of administration of the CI-977 begins at least thirty minutes before the general anesthesia.

16. A method as recited in claim 9, wherein the CI-977 is administered intramuscularly or subcutaneously prior to the general anesthesia.

* * * * *